US007781197B2

(12) United States Patent
Reski et al.

(10) Patent No.: US 7,781,197 B2
(45) Date of Patent: *Aug. 24, 2010

(54) TRANSFORMED BRYOPHYTE CELL HAVING DISRUPTED ENDOGENOUS ALPHA 1,3-FUCOSYL AND BETA 1,2-XYLOSYL TRANSFERASE ENCODING NUCLEOTIDE SEQUENCES FOR THE PRODUCTION OF HETEROLOGOUS GLYCOSYLATED PROTEINS

(75) Inventors: Ralf Reski, Oberried-Zastler (DE); Gilbert Gorr, Freiburg (DE); Eva Decker, Freiburg (DE); Christian Stemmer, Freiburg (DE); Otmar Lienhart, Freiburg (DE); Anna Koprivova, Freiburg (DE)

(73) Assignee: greenovation Biotech GmbH, Freiburg (DE)

( * ) Notice: Subject to any disclaimer, the term of this patent is extended or adjusted under 35 U.S.C. 154(b) by 430 days.

This patent is subject to a terminal disclaimer.

(21) Appl. No.: 10/539,725

(22) PCT Filed: Dec. 18, 2003

(86) PCT No.: PCT/EP03/14576

§ 371 (c)(1),
(2), (4) Date: Jun. 20, 2005

(87) PCT Pub. No.: WO2004/057002

PCT Pub. Date: Jul. 8, 2004

(65) Prior Publication Data
US 2008/0141387 A1    Jun. 12, 2008

(30) Foreign Application Priority Data
Dec. 20, 2002 (EP) .................................. 02028536
Oct. 7, 2003 (EP) .................................. 03022453

(51) Int. Cl.
*C12N 9/10* (2006.01)
*C12N 5/04* (2006.01)
*C12N 15/82* (2006.01)

(52) U.S. Cl. ........................ 435/193; 435/419; 435/468; 800/278

(58) Field of Classification Search ........................ None
See application file for complete search history.

(56) References Cited
U.S. PATENT DOCUMENTS
2008/0201804 A1 * 8/2008 Gorr et al. .................. 800/298

FOREIGN PATENT DOCUMENTS
WO    01/25456 A2    4/2001
WO    01/29242 A2    4/2001

OTHER PUBLICATIONS

Schaefer et al., The Moss *Physcomitrella patens*, Now and Then. Plant Physiol., 2001, vol. 127: 1430-1438.*
Kisselev L., Polypeptide release factors in prokaryotes and eukaryotes: same function, different structure. Structure, 2002, vol. 10: 8-9.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of a b-ketoacyl synthase to a malonyl decarboxylase by replacement of the active-site cysteine with glutamine. Biochemistry, 1999, vol. 38: 11643-11650.*
Bennett et al., Cloning and characterization of a close homolgue of human UDP-N-acetyl-a-D-galactosamine: Polypeptide N-acetylgalactosaminyltransferase-T3, designated as GalNAc-T6. J. Biol. Chem., 1999, vol. 274 (36): 25362-25370.*
Jenkins et al., Getting the glycosylation right: Implications for the biotechnology industry. Nature Biotechnol., 1996, vol. 14: 975-961.*
Reski et al.; Genome analysis of the moss *Physcomitrella patens* (Hedw.) B.S.G.; Mol Gen Genet; 1994; vol. 244; pp. 352-359.
Engel; The Induction of Biochemical and Morphological Mutants in the Moss *Physcomitrella patens*; Amer J. Bot; 1968; vol. 55(4); pp. 438-446.
Töpfer et al.; NAR 15; 1987; p. 589; IRL Press Limited Oxford England.
Reski et al.; Induction of budding on chloronemata and caulonemata of the moss, *Physcomitrella patens*, using isopentenyladenine; Planta; 1985; vol. 165; pp. 354-358.
Schaefer; Principles and protocols for the moss *Physcomitrella patens*; Institute of Ecology; Laboratory of Plant Cell Genetics; University of Lausanne; May 2001; pp. 1-14.
Schaefer et al.; Stable transformation of the moss *Physcomitrella patens*; Mol Gen Genet; 1991; vol. 226; pp. 418-424.
Reski et al.; Production of a heterologous protein in bioreactor cultures of fully differentiated moss plants; Plant Tissue and Biotechnology; Sep. 1996; vol. 2; No. 3; pp. 142-147.
Strepp et al.; Plant nuclear gene knockout reveals a role in plastid division for the homolog of the bacterial cell division protein FtsZ, an ancestral tublin; Proc. Natl. Acad. Sci. USA; Apr. 1998; vol. 95; pp. 4368-4373.
Wilson et al.; Analysis of Asn-linked glycans from vegetable foodstuffs: wiespread occurrence of Lewis a, core . . . ; Glycobiology; 2001; vol. 11; No. 4; pp. 261-274.
Koprivova et al.; Functional Knockout of the Adenosine 5'-Phosphosulfate Reductase Gene in *Physcomitrella patens* Revives an Old Route of Sulfate Assimilation; The Journal of Boiological Chemistry; 2002; vol. 277, No. 35; pp. 32195-32201.
Kiessling et al.; Visualization of a Cytoskeleton-like FtsZ Network in Chloroplasts; JCB Report; 2000; vol. 151, No. 4; pp. 945-950.
Schafer et al.; Efficient gene targeting in the moss *Physcomitrella patens*; The Plant Journal; 1997; vol. 11; No. 6; Jun. 1997; pp. 1195-1206.

(Continued)

*Primary Examiner*—Ganapathirama Raghu
(74) *Attorney, Agent, or Firm*—Biotech Beach Law Group PC; Raymond Wagenknecht

(57) ABSTRACT

Bryophyte plants and bryophyte plant cells comprising dysfunctional fucT and xylT genes and an introduced glycosyltransferase gene, methods for the production of glycosylated proteins therewith, vectors and uses thereof.

12 Claims, No Drawings

OTHER PUBLICATIONS

Lerouge et al.; N-Glycoprotein biosynthesis in plants: recent developments and future trends; 1998; vol. 38; pp. 31-48.

International Search Report (PCT/ISA/210); PCT/EP2003/14576; completed May 25, 2004.

Schaewen et al, Isolation of a mutant *Arabidopsis* plant that lacks n-acetyl glucosaminyl transferase I and is unable to synthesize golgi-modified complex n-linked glycans, Plant Physiol 102:1109-1118 (1993).

Bakker et al, Plant members of the alpha1-3/4-fucosyltransferase gene family encode an alpha1-4 fucsoyltransferase, potentially involved in Lewis biosynthesis, and two core alpha1-3 fucosyltransferases, FEBS Letters 507:304-312 (2001).

Koprivova et al., Targeted knockouts of *Physcomitrella* lacking plant-specific immunogenic N-glycans, Plant Biotechnology Journal 2:517-523 (2004).

* cited by examiner

SEQUENCE LISTING

<160> NUMBER OF SEQ ID NOS: 89

<210> SEQ ID NO 1
<211> LENGTH: 36
<212> TYPE: DNA
<213> ORGANISM: Artificial
<220> FEATURE:
<223> OTHER INFORMATION: Primer sequence MoB323

<400> SEQUENCE: 1
atactcgagg aagatgaact tttctgcctg tcttgg                                36

<210> SEQ ID NO 2
<211> LENGTH: 26
<212> TYPE: DNA
<213> ORGANISM: Artificial
<220> FEATURE:
<223> OTHER INFORMATION: Primer sequence MoB349

<400> SEQUENCE: 2
ctgccatggg tgcagcctgg gaccac                                           26

<210> SEQ ID NO 3
<211> LENGTH: 23
<212> TYPE: DNA
<213> ORGANISM: Artificial
<220> FEATURE:
<223> OTHER INFORMATION: Primer sequence GNT(d)1
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 3
gtngcngcng tngtngtnat ggc                                              23

<210> SEQ ID NO 4
<211> LENGTH: 27
<212> TYPE: DNA
<213> ORGANISM: Artificial
<220> FEATURE:
<223> OTHER INFORMATION: Primer sequence GTN(d)3
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

```
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 4
ccyttrtang cngcnctgng gnacncc                                      27

<210> SEQ ID NO 5
<211> LENGTH: 25
<212> TYPE: DNA
<213> ORGANISM: Artificial
<220> FEATURE:
<223> OTHER INFORMATION: Primer sequence GTN(d)2
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 5
tayaaratnc agncaytaya artgg                                        25

<210> SEQ ID NO 6
<211> LENGTH: 23
<212> TYPE: DNA
<213> ORGANISM: Artificial
<220> FEATURE:
<223> OTHER INFORMATION: Primer sequence GTN(d)4
<220> FEATURE:
<221> NAME/KEY: misc_feature
<222> LOCATION: (21)..(21)
<223> OTHER INFORMATION: n is a, c, g, or t

<400> SEQUENCE: 6
arrtaytgyt traaraaytg ncc                                          23

<210> SEQ ID NO 7
<211> LENGTH: 20
<212> TYPE: DNA
<213> ORGANISM: Artificial
<220> FEATURE:
<223> OTHER INFORMATION: Primer sequence 5RACEG3

<400> SEQUENCE: 7
gtccgtgtcc aataaaggag                                              20

<210> SEQ ID NO 8
<211> LENGTH: 21
<212> TYPE: DNA
<213> ORGANISM: Artificial
<220> FEATURE:
<223> OTHER INFORMATION: Primer sequence 5RACEG4

<400> SEQUENCE: 8
```
gtcgggagag atttccatgt c					21

<210> SEQ ID NO 9
<211> LENGTH: 20
<212> TYPE: DNA
<213> ORGANISM: Artificial
<220> FEATURE:
<223> OTHER INFORMATION: Primer sequence 5RACEG5

<400> SEQUENCE: 9
ctaagatgac gacccttcgg					20

<210> SEQ ID NO 10
<211> LENGTH: 22
<212> TYPE: DNA
<213> ORGANISM: Artificial
<220> FEATURE:
<223> OTHER INFORMATION: Primer sequence 5RACE6

<400> SEQUENCE: 10
catcctgaga acaaaaagt gg					22

<210> SEQ ID NO 11
<211> LENGTH: 21
<212> TYPE: DNA
<213> ORGANISM: Artificial
<220> FEATURE:
<223> OTHER INFORMATION: Primer sequence 5RACE7

<400> SEQUENCE: 11
agttacagac ttcaatgtac g					21

<210> SEQ ID NO 12
<211> LENGTH: 20
<212> TYPE: DNA
<213> ORGANISM: Artificial
<220> FEATURE:
<223> OTHER INFORMATION: Primer sequence 5RACE8

<400> SEQUENCE: 12
aatcaggacg gttgcaagcc					20

<210> SEQ ID NO 13
<211> LENGTH: 20
<212> TYPE: DNA
<213> ORGANISM: Artificial
<220> FEATURE:
<223> OTHER INFORMATION: Primer sequence 3RACEG1

<400> SEQUENCE: 13
ttatccgacc tgaagtttgc					20

<210> SEQ ID NO 14
<211> LENGTH: 20
<212> TYPE: DNA
<213> ORGANISM: Artificial
<220> FEATURE:
<223> OTHER INFORMATION: Primer sequence 3RACEG2

<400> SEQUENCE: 14
gacctacaat tttggagagc					20

<210> SEQ ID NO 15
<211> LENGTH: 20
<212> TYPE: DNA
<213> ORGANISM: Artificial

```
<220> FEATURE:
<223> OTHER INFORMATION: Primer sequence GNT5F

<400> SEQUENCE: 15
tgggctttaa cacaactttt                                              20

<210> SEQ ID NO 16
<211> LENGTH: 19
<212> TYPE: DNA
<213> ORGANISM: Artificial
<220> FEATURE:
<223> OTHER INFORMATION: Primer sequence GTN6R

<400> SEQUENCE: 16
gccctaagct tgatccctg                                               19

<210> SEQ ID NO 17
<211> LENGTH: 21
<212> TYPE: DNA
<213> ORGANISM: Artificial
<220> FEATURE:
<223> OTHER INFORMATION: Primer sequence GNT21F

<400> SEQUENCE: 17
atggcagata tggctcgatt g                                            21

<210> SEQ ID NO 18
<211> LENGTH: 22
<212> TYPE: DNA
<213> ORGANISM: Artificial
<220> FEATURE:
<223> OTHER INFORMATION: Primer sequence GNT15R

<400> SEQUENCE: 18
agtttctatg gtatctaact gc                                           22

<210> SEQ ID NO 19
<211> LENGTH: 21
<212> TYPE: DNA
<213> ORGANISM: Artificial
<220> FEATURE:
<223> OTHER INFORMATION: Primer sequence GNTHT7

<400> SEQUENCE: 19
gagcatccaa gcttgacctg g                                            21

<210> SEQ ID NO 20
<211> LENGTH: 22
<212> TYPE: DNA
<213> ORGANISM: Artificial
<220> FEATURE:
<223> OTHER INFORMATION: Primer sequence GNTET7

<400> SEQUENCE: 20
gcaccgtgaa ttcttctagc tt                                           22

<210> SEQ ID NO 21
<211> LENGTH: 23
<212> TYPE: DNA
<213> ORGANISM: Artificial
<220> FEATURE:
<223> OTHER INFORMATION: Primer sequence GNTHT3

<400> SEQUENCE: 21
ggaagaacaa gcttcaaagt ggc                                          23
```

```
<210> SEQ ID NO 22
<211> LENGTH: 21
<212> TYPE: DNA
<213> ORGANISM: Artificial
<220> FEATURE:
<223> OTHER INFORMATION: Primer sequence GNTPT3

<400> SEQUENCE: 22
gatccctgca gatctcaaac g                                              21

<210> SEQ ID NO 23
<211> LENGTH: 19
<212> TYPE: DNA
<213> ORGANISM: Artificial
<220> FEATURE:
<223> OTHER INFORMATION: Primer sequence GNT7F

<400> SEQUENCE: 23
gttcsatggt ttgagcagg                                                 19

<210> SEQ ID NO 24
<211> LENGTH: 19
<212> TYPE: DNA
<213> ORGANISM: Artificial
<220> FEATURE:
<223> OTHER INFORMATION: Primer sequence GNT8R

<400> SEQUENCE: 24
gcgacctttc ctattctcc                                                 19

<210> SEQ ID NO 25
<211> LENGTH: 20
<212> TYPE: DNA
<213> ORGANISM: Artificial
<220> FEATURE:
<223> OTHER INFORMATION: Primer sequence N1

<400> SEQUENCE: 25
taccgacagt ggtcccaaag                                                20

<210> SEQ ID NO 26
<211> LENGTH: 20
<212> TYPE: DNA
<213> ORGANISM: Artificial
<220> FEATURE:
<223> OTHER INFORMATION: Primer sequence N2

<400> SEQUENCE: 26
ccaccatgat attcggcaag                                                20

<210> SEQ ID NO 27
<211> LENGTH: 20
<212> TYPE: DNA
<213> ORGANISM: Artificial
<220> FEATURE:
<223> OTHER INFORMATION: Primer sequence GNT5F

<400> SEQUENCE: 27
tgggctttaa cacaactttt                                                20

<210> SEQ ID NO 28
<211> LENGTH: 19
<212> TYPE: DNA
<213> ORGANISM: Artificial
<220> FEATURE:
<223> OTHER INFORMATION: Primer sequence N3
```

```
<400> SEQUENCE: 28
tgtcgtgctc caccatgtt                                              19

<210> SEQ ID NO 29
<211> LENGTH: 18
<212> TYPE: DNA
<213> ORGANISM: Artificial
<220> FEATURE:
<223> OTHER INFORMATION: Primer sequence N4

<400> SEQUENCE: 29
gttgagcata taagaaac                                               18

<210> SEQ ID NO 30
<211> LENGTH: 22
<212> TYPE: DNA
<213> ORGANISM: Artificial
<220> FEATURE:
<223> OTHER INFORMATION: Primer sequence GNT10R

<400> SEQUENCE: 30
cacattgttc aatttgatag ac                                          22

<210> SEQ ID NO 31
<211> LENGTH: 21
<212> TYPE: DNA
<213> ORGANISM: Artificial
<220> FEATURE:
<223> OTHER INFORMATION: Primer sequence FD4F
<220> FEATURE:
<221> NAME/KEY: misc_feature
<222> LOCATION: (6)..(6)
<223> OTHER INFORMATION: n is a, c, g, or t

<400> SEQUENCE: 31
tgggcngart aygayatgat g                                           21

<210> SEQ ID NO 32
<211> LENGTH: 23
<212> TYPE: DNA
<213> ORGANISM: Artificial
<220> FEATURE:
<223> OTHER INFORMATION: Primer sequence FDR1
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 32
tgngtnarnc cnadnggrta dat                                         23

<210> SEQ ID NO 33
```

<211> LENGTH: 17
<212> TYPE: DNA
<213> ORGANISM: Artificial
<220> FEATURE:
<223> OTHER INFORMATION: Primer sequence FD5R
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 33
tgnacngcng ccatrtc                                                    17

<210> SEQ ID NO 34
<211> LENGTH: 18
<212> TYPE: DNA
<213> ORGANISM: Artificial
<220> FEATURE:
<223> OTHER INFORMATION: Primer sequence 5FT4

<400> SEQUENCE: 34
gtaacattcg cataatgg                                                   18

<210> SEQ ID NO 35
<211> LENGTH: 19
<212> TYPE: DNA
<213> ORGANISM: Artificial
<220> FEATURE:
<223> OTHER INFORMATION: Primer sequence 5FT5

<400> SEQUENCE: 35
cgatcattat gcgcaccac                                                  19

<210> SEQ ID NO 36
<211> LENGTH: 18
<212> TYPE: DNA
<213> ORGANISM: Artificial
<220> FEATURE:
<223> OTHER INFORMATION: Primer sequence 5FT6

<400> SEQUENCE: 36
ggaaataaaa gcagctcc                                                   18

<210> SEQ ID NO 37
<211> LENGTH: 19
<212> TYPE: DNA
<213> ORGANISM: Artificial
<220> FEATURE:
<223> OTHER INFORMATION: Primer sequence 5FT7

<400> SEQUENCE: 37
agggtgaatc tccatagcc                                                  19

<210> SEQ ID NO 38
<211> LENGTH: 19
<212> TYPE: DNA
<213> ORGANISM: Artificial
<220> FEATURE:
<223> OTHER INFORMATION: Primer sequence 5FT8

<400> SEQUENCE: 38

-continued catctgcctg accctcacc                                                19

<210> SEQ ID NO 39
<211> LENGTH: 18
<212> TYPE: DNA
<213> ORGANISM: Artificial
<220> FEATURE:
<223> OTHER INFORMATION: Primer sequence 5FT9

<400> SEQUENCE: 39
gccttgaaca cgcatggc                                                 18

<210> SEQ ID NO 40
<211> LENGTH: 18
<212> TYPE: DNA
<213> ORGANISM: Artificial
<220> FEATURE:
<223> OTHER INFORMATION: Primer sequence 5FT10

<400> SEQUENCE: 40
cgatacaacc agcacagg                                                 18

<210> SEQ ID NO 41
<211> LENGTH: 19
<212> TYPE: DNA
<213> ORGANISM: Artificial
<220> FEATURE:
<223> OTHER INFORMATION: Primer sequence 5FT11

<400> SEQUENCE: 41
cttctctagc cattctgcc                                                19

<210> SEQ ID NO 42
<211> LENGTH: 20
<212> TYPE: DNA
<213> ORGANISM: Artificial
<220> FEATURE:
<223> OTHER INFORMATION: Primer sequence 3FT1

<400> SEQUENCE: 42
gcagtggaag tttaatggtc                                               20

<210> SEQ ID NO 43
<211> LENGTH: 21
<212> TYPE: DNA
<213> ORGANISM: Artificial
<220> FEATURE:
<223> OTHER INFORMATION: Primer sequence 3FT2

<400> SEQUENCE: 43
tcgtttctag ctctagtaga c                                             21

<210> SEQ ID NO 44
<211> LENGTH: 18
<212> TYPE: DNA
<213> ORGANISM: Artificial
<220> FEATURE:
<223> OTHER INFORMATION: Primer sequence FTA9F

<400> SEQUENCE: 44
atgctcccag cccaagac                                                 18

<210> SEQ ID NO 45
<211> LENGTH: 21
<212> TYPE: DNA

```
<213> ORGANISM: Artificial
<220> FEATURE:
<223> OTHER INFORMATION: Primer sequence FTA10R

<400> SEQUENCE: 45
tgtctactag agctagaaac g                                              21

<210> SEQ ID NO 46
<211> LENGTH: 20
<212> TYPE: DNA
<213> ORGANISM: Artificial
<220> FEATURE:
<223> OTHER INFORMATION: Primer sequence FT18F

<400> SEQUENCE: 46
tagggagtaa atatgaaggg                                                20

<210> SEQ ID NO 47
<211> LENGTH: 21
<212> TYPE: DNA
<213> ORGANISM: Artificial
<220> FEATURE:
<223> OTHER INFORMATION: Primer sequence FTA12R

<400> SEQUENCE: 47
tacttccaat tgaagacaag g                                              21

<210> SEQ ID NO 48
<211> LENGTH: 18
<212> TYPE: DNA
<213> ORGANISM: Artificial
<220> FEATURE:
<223> OTHER INFORMATION: Primer sequence FT15F

<400> SEQUENCE: 48
aatgttctgt gccatgcg                                                  18

<210> SEQ ID NO 49
<211> LENGTH: 19
<212> TYPE: DNA
<213> ORGANISM: Artificial
<220> FEATURE:
<223> OTHER INFORMATION: Primer sequence FT16R

<400> SEQUENCE: 49
tgcttcaaat gggctaggg                                                 19

<210> SEQ ID NO 50
<211> LENGTH: 28
<212> TYPE: DNA
<213> ORGANISM: Artificial
<220> FEATURE:
<223> OTHER INFORMATION: Primer sequence nptII/NdeI-F

<400> SEQUENCE: 50
atgccatatg gcatgcctgc aggtcaac                                       28

<210> SEQ ID NO 51
<211> LENGTH: 29
<212> TYPE: DNA
<213> ORGANISM: Artificial
<220> FEATURE:
<223> OTHER INFORMATION: Primer sequence nptII/BstZ17I-R

<400> SEQUENCE: 51
gcatgtatac gcatgcctgc aggtcactg                                      29
```

<210> SEQ ID NO 52
<211> LENGTH: 19
<212> TYPE: DNA
<213> ORGANISM: Artificial
<220> FEATURE:
<223> OTHER INFORMATION: Primer sequence FT14F

<400> SEQUENCE: 52
acaaagttac atactcgcg                                                19

<210> SEQ ID NO 53
<211> LENGTH: 20
<212> TYPE: DNA
<213> ORGANISM: Artificial
<220> FEATURE:
<223> OTHER INFORMATION: Primer sequence R10

<400> SEQUENCE: 53
tctttcacta ttcggtgacg                                               20

<210> SEQ ID NO 54
<211> LENGTH: 19
<212> TYPE: DNA
<213> ORGANISM: Artificial
<220> FEATURE:
<223> OTHER INFORMATION: Primer sequence R11

<400> SEQUENCE: 54
cgaccacaac attagatcc                                                19

<210> SEQ ID NO 55
<211> LENGTH: 23
<212> TYPE: DNA
<213> ORGANISM: Artificial
<220> FEATURE:
<223> OTHER INFORMATION: Primer sequence XDF1
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 55
tgygargsnt ayttyggnaa ygg                                           23

<210> SEQ ID NO 56
<211> LENGTH: 23
<212> TYPE: DNA
<213> ORGANISM: Artificial
<220> FEATURE:
<223> OTHER INFORMATION: Primer sequence XDR1
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 56

```
gcncknayca tytcnccraa ytc                                           23

<210> SEQ ID NO 57
<211> LENGTH: 23
<212> TYPE: DNA
<213> ORGANISM: Artificial
<220> FEATURE:
<223> OTHER INFORMATION: Primer sequence XDF2
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 57
ggnggngara arytngarra ngt                                           23

<210> SEQ ID NO 58
<211> LENGTH: 18
<212> TYPE: DNA
<213> ORGANISM: Artificial
<220> FEATURE:
<223> OTHER INFORMATION: Primer sequence 5XT1

<400> SEQUENCE: 58
tcctccttct ctgggacc                                                 18

<210> SEQ ID NO 59
<211> LENGTH: 21
<212> TYPE: DNA
<213> ORGANISM: Artificial
<220> FEATURE:
<223> OTHER INFORMATION: Primer sequence 5XT2

<400> SEQUENCE: 59
agctccagtt gtgaaatatg g                                             21

<210> SEQ ID NO 60
<211> LENGTH: 18
<212> TYPE: DNA
<213> ORGANISM: Artificial
<220> FEATURE:
<223> OTHER INFORMATION: Primer sequence 5XT4

<400> SEQUENCE: 60
cttccttcac cacactac                                                 18

<210> SEQ ID NO 61
<211> LENGTH: 18
<212> TYPE: DNA
<213> ORGANISM: Artificial
<220> FEATURE:
<223> OTHER INFORMATION: Primer sequence 5XT5

<400> SEQUENCE: 61
tagcatgact gtgtggcc                                                 18
```

```
<210> SEQ ID NO 62
<211> LENGTH: 18
<212> TYPE: DNA
<213> ORGANISM: Artificial
<220> FEATURE:
<223> OTHER INFORMATION: Primer sequence 5XT6

<400> SEQUENCE: 62
aaaggcttga gtgtagcc                                                 18

<210> SEQ ID NO 63
<211> LENGTH: 19
<212> TYPE: DNA
<213> ORGANISM: Artificial
<220> FEATURE:
<223> OTHER INFORMATION: Primer sequence 3XT1

<400> SEQUENCE: 63
gcctttcttg cacgggttg                                                19

<210> SEQ ID NO 64
<211> LENGTH: 19
<212> TYPE: DNA
<213> ORGANISM: Artificial
<220> FEATURE:
<223> OTHER INFORMATION: Primer sequence 3XT2

<400> SEQUENCE: 64
ggacattcca ataatccc                                                 19

<210> SEQ ID NO 65
<211> LENGTH: 19
<212> TYPE: DNA
<213> ORGANISM: Artificial
<220> FEATURE:
<223> OTHER INFORMATION: Primer sequence XT15R

<400> SEQUENCE: 65
gtcctgttaa atgccttgc                                                19

<210> SEQ ID NO 66
<211> LENGTH: 20
<212> TYPE: DNA
<213> ORGANISM: Artificial
<220> FEATURE:
<223> OTHER INFORMATION: Primer sequence XT-M1F

<400> SEQUENCE: 66
aggttgagca atcatatggc                                               20

<210> SEQ ID NO 67
<211> LENGTH: 20
<212> TYPE: DNA
<213> ORGANISM: Artificial
<220> FEATURE:
<223> OTHER INFORMATION: Primer sequence XT11R

<400> SEQUENCE: 67
atcccagaaa tatctgatcc                                               20

<210> SEQ ID NO 68
<211> LENGTH: 18
<212> TYPE: DNA
<213> ORGANISM: Artificial
<220> FEATURE:
<223> OTHER INFORMATION: Primer sequence XT12F
```

<400> SEQUENCE: 68
tgtgaggcgt ctttggc                                                   18

<210> SEQ ID NO 69
<211> LENGTH: 29
<212> TYPE: DNA
<213> ORGANISM: Artificial
<220> FEATURE:
<223> OTHER INFORMATION: Primer sequence nptII/SalI-F

<400> SEQUENCE: 69
atgcgtcgac gtcaacatgg tggagcacg                                      29

<210> SEQ ID NO 70
<211> LENGTH: 31
<212> TYPE: DNA
<213> ORGANISM: Artificial
<220> FEATURE:
<223> OTHER INFORMATION: Primer sequence nptII/NdeI-R

<400> SEQUENCE: 70
gcatcatatg tcactggatt ttggttttag g                                   31

<210> SEQ ID NO 71
<211> LENGTH: 20
<212> TYPE: DNA
<213> ORGANISM: Artificial
<220> FEATURE:
<223> OTHER INFORMATION: Primer sequence XT13R

<400> SEQUENCE: 71
acgatccaaa atctggacgc                                                20

<210> SEQ ID NO 72
<211> LENGTH: 32
<212> TYPE: DNA
<213> ORGANISM: Artificial
<220> FEATURE:
<223> OTHER INFORMATION: Primer sequence GalTXh-F

<400> SEQUENCE: 72
ttctcgagac aatgaggctt cgggagccgc tc                                  32

<210> SEQ ID NO 73
<211> LENGTH: 30
<212> TYPE: DNA
<213> ORGANISM: Artificial
<220> FEATURE:
<223> OTHER INFORMATION: Primer sequence GalTXb-R

<400> SEQUENCE: 73
ggtctagact agctcggtgt cccgatgtcc                                     30

<210> SEQ ID NO 74
<211> LENGTH: 30
<212> TYPE: DNA
<213> ORGANISM: Artificial
<220> FEATURE:
<223> OTHER INFORMATION: Primer sequence XTB-F

<400> SEQUENCE: 74
ttggatcctc aattacgaag cacaccatgc                                     30

<210> SEQ ID NO 75
<211> LENGTH: 32

```
<212> TYPE: DNA
<213> ORGANISM: Artificial
<220> FEATURE:
<223> OTHER INFORMATION: Primer sequence XTB-R

<400> SEQUENCE: 75
ttggatcctc ctcccagaaa catctgatcc ag                              32

<210> SEQ ID NO 76
<211> LENGTH: 28
<212> TYPE: DNA
<213> ORGANISM: Artificial
<220> FEATURE:
<223> OTHER INFORMATION: Primer sequence MoB521

<400> SEQUENCE: 76
ttgccgctat ctacttgtat gctaacgt                                   28

<210> SEQ ID NO 77
<211> LENGTH: 25
<212> TYPE: DNA
<213> ORGANISM: Artificial
<220> FEATURE:
<223> OTHER INFORMATION: Primer sequence MoB575

<400> SEQUENCE: 77
tgccgtggat gtgctagata atctt                                      25

<210> SEQ ID NO 78
<211> LENGTH: 33
<212> TYPE: DNA
<213> ORGANISM: Artificial
<220> FEATURE:
<223> OTHER INFORMATION: Primer sequence FTB-F

<400> SEQUENCE: 78
taggatccag atgatgtctg ctcggcagaa tgg                             33

<210> SEQ ID NO 79
<211> LENGTH: 33
<212> TYPE: DNA
<213> ORGANISM: Artificial
<220> FEATURE:
<223> OTHER INFORMATION: Primer sequence FTB-R

<400> SEQUENCE: 79
ctggatcctt gtagatccga aggtctgagt tcc                             33

<210> SEQ ID NO 80
<211> LENGTH: 26
<212> TYPE: DNA
<213> ORGANISM: Artificial
<220> FEATURE:
<223> OTHER INFORMATION: Primer sequence MoB435

<400> SEQUENCE: 80
tcctacctgc ggagcaacag atattg                                     26

<210> SEQ ID NO 81
<211> LENGTH: 27
<212> TYPE: DNA
<213> ORGANISM: Artificial
<220> FEATURE:
<223> OTHER INFORMATION: Primer sequence MoB495

<400> SEQUENCE: 81
```

| | |
|---|---|
| gtggacccag atttgctggt gcacttg | 27 |

<210> SEQ ID NO 82
<211> LENGTH: 18
<212> TYPE: DNA
<213> ORGANISM: Artificial
<220> FEATURE:
<223> OTHER INFORMATION: Primer sequence XT14F

<400> SEQUENCE: 82

| | |
|---|---|
| ttacgaagca caccatgc | 18 |

<210> SEQ ID NO 83
<211> LENGTH: 19
<212> TYPE: DNA
<213> ORGANISM: Artificial
<220> FEATURE:
<223> OTHER INFORMATION: Primer sequence 5XT3

<400> SEQUENCE: 83

| | |
|---|---|
| ttcttcctca tttcgtccc | 19 |

<210> SEQ ID NO 84
<211> LENGTH: 35
<212> TYPE: DNA
<213> ORGANISM: Artificial
<220> FEATURE:
<223> OTHER INFORMATION: Primer sequence MoB558

<400> SEQUENCE: 84

| | |
|---|---|
| gttccgcggt gatcccgttt tcatatcagt gtatt | 35 |

<210> SEQ ID NO 85
<211> LENGTH: 36
<212> TYPE: DNA
<213> ORGANISM: Artificial
<220> FEATURE:
<223> OTHER INFORMATION: Primer sequence MoB557

<400> SEQUENCE: 85

| | |
|---|---|
| tttgagctct acgtaacaat aacataaaat atcaca | 36 |

<210> SEQ ID NO 86
<211> LENGTH: 815
<212> TYPE: DNA
<213> ORGANISM: Artificial
<220> FEATURE:
<223> OTHER INFORMATION: PCR product

<400> SEQUENCE: 86

| | |
|---|---|
| gttccgcggt gatcccgttt tcatatcagt gtattatcat cagtgactgc atattgacac | 60 |
| ccaattctga tgattttta tttttattt tttattttt ttggtatggt tacatgcttt | 120 |
| tcagaggttt ctatgccgct gagtattttc ctgaatcgcg aggtgtgaca ggttatctgc | 180 |
| gccgtccacc caatatttta tgatgagtcg atgattcgtg agactaatct agcttaacct | 240 |
| ttttcttact ggcaagtcaa aattgagttt aaaatatttc agtatcctgt tagtaatttc | 300 |
| agacacatgt attctatgtc tcatactctt tacgtgaaag ttcaactgac ttatattttg | 360 |
| tcgtttttct gtagatcact gttttagcgc atacaaagac aattgtctaa atattttaa | 420 |
| agaaggtgat atttattat aagatagaag tcaatatgtt ttttgttat gcacatgact | 480 |
| tgaataaaat aaatttttt gttagattta aatactttt gaattatagc tttgttgaaa | 540 |
| ttaaggaatt tatattcata agaagctact cgaacaaatt tacaaagaga acatttgata | 600 |

-continued

```
agtaaaagta attaaaagtt tttttttaatt taaaaagatt aattttttatt aataagaaga        660 acttggaaag ttagaaaaat atttaactttt aaaaattaag aaaacaaggc aaaactttaa        720
tttacaaata cttaatgtag attaattttc ttattatata ttagcacaaa ttatcattat        780
gtgatatttt atgttattgt tacgtagagc tcaaa                                   815

<210> SEQ ID NO 87
<211> LENGTH: 34
<212> TYPE: DNA
<213> ORGANISM: Artificial
<220> FEATURE:
<223> OTHER INFORMATION: Primer sequence MoB555

<400> SEQUENCE: 87
cgcgttaact ctctctatct ctctctgtgt tgcg                                    34

<210> SEQ ID NO 88
<211> LENGTH: 32
<212> TYPE: DNA
<213> ORGANISM: Artificial
<220> FEATURE:
<223> OTHER INFORMATION: Primer sequence MoB556

<400> SEQUENCE: 88
cgagaattct cacttagaag aagcccaatc ct                                      32

<210> SEQ ID NO 89
<211> LENGTH: 882
<212> TYPE: DNA
<213> ORGANISM: Artificial
<220> FEATURE:
<223> OTHER INFORMATION: PCR product

<400> SEQUENCE: 89
cgcgttaact ctctctatct ctctctgtgt tgcgtttgat caggggtttt agggtttggg         60
tccagggttc cgaggagtat cgtcacgtgt attgcggtct tgttggagat tcctcagttg        120
tgcatgtaga tataaactta gtttagtcca cgatcggttt ctaatcgtgg atttttgtgg        180
gtttcggtcg ttgagcaaga attttgtgaa tttttttgtat tgggggaagg aaatggggtt       240
atggcgatat cgtttttcgtt gggttcaacg tgatcggtga gctccaggaa gggctggtca       300
ctcacaatcc ggtattcgtc tcatcgagac gcatttatcg gttcattata tgtatatata       360
tatatatata tatatgcaga gtcgattgtg ttgcaatttc tgaactaggt actgttgaat        420
tgtagattgc cttcaagtag ctctcgatgt tggaatgacg sacacaaatt ctgctactga        480
atgagaccat attctgcacc gttaattggt tttatgaata tatggtgtcg aattacattc        540
tgtctcgaat ccatgcgccc tttctgcacg aacgttggtt tgtagttgta gtgcagccag        600
tgtgtttggt ttaggattat gctttgacga tcgatgagtc cgtttcatgg ttttatactt        660
gtcatttatc ttcttgtgat tttttgtta caaatgttcc cccaattgta acgtgggact         720
ttcgtgtgtg gtggttgctc aaattgatag ttttggtcat ttgatttgcg gagagcaatc       780
ggtgtcatgg aaaatcccctt cgactgcttt gatccaatca aagttctgct tgagccaatg      840
tgagaggtgg aggattgggc ttcttctaag tgagaattct cg                           882
```

TRANSFORMED BRYOPHYTE CELL HAVING DISRUPTED ENDOGENOUS ALPHA 1,3-FUCOSYL AND BETA 1,2-XYLOSYL TRANSFERASE ENCODING NUCLEOTIDE SEQUENCES FOR THE PRODUCTION OF HETEROLOGOUS GLYCOSYLATED PROTEINS

This is a National Phase Application in the United States of International Patent Application No. PCT/EP2003/014576, filed Dec. 18, 2003, which claims priority on European Patent Application No. 02028536.7, filed Dec. 20, 2002 and European Patent Application No. 03022453.9, filed Oct. 7, 2003. The entire disclosures of the above patent applications are hereby incorporated by reference.

BACKGROUND

The present invention relates to a method for producing heterologous glycosylated proteins in bryophyte cells, such as in transformed *Physcomitrella patens* cells in culture. In particular, the method relates to a method for producing glycosylated proteins comprising animal glycosylation patterns, such as pharmaceutical proteins for use in mammals, including humans, in bryophyte cells such as *Physcomitrella patens* cells, the genetic material required therefore, such as DNA and RNA, vectors, host cells, methods of introduction of genetic material there into, and uses thereof.

In the past, heterologous proteins have been produced using a variety of transformed cell systems, such as those derived from bacteria, fungi, such as yeasts, insect, plant or mammalian cell lines (Kudo T. 1994, In: Y. Murooka and T. Amanaka (Eds.) Recombinant microbes for industrial and agricultural applications, pp. 291-299, Marcel Dekker, New York; Harashima S., Bioproc. Technol. 1994, 19: 137-158; Archer D. B. 1994, In: Y. Murooka and T. Amanaka (Eds.) Recombinant microbes for industrial and agricultural applications, pp. 373-393, Marcel Dekker, New York; Goosen M. F. A. 1993, In: M. F. A. Goosen, A. Baugulis and P. Faulkner (Eds.) Insect cell culture engineering, pp. 1-16, Marcel Dekker, New York; Hesse F. & Wagner R., Trends in Biotechnol. 2000, 18(4): 173-180).

Proteins produced in prokaryotic organisms may not be post-translationally modified in a similar manner to that of eukaryotic proteins produced in eukaryotic systems, e.g. they may not be glycosylated with appropriate sugars at particular amino acid residues, such as aspartic acid (N) residues (N-linked glycosylation). Furthermore, folding of bacterially-produced eukaryotic proteins may be inappropriate due to, for example, the inability of the bacterium to form cysteine disulfide bridges. Moreover, bacterially-produced recombinant proteins frequently aggregate and accumulate as insoluble inclusion bodies.

Eukaryotic cell systems are better suited for the production of glycosylated proteins found in various eukaryotic organisms, such as humans, since such cell systems may effect post-translational modifications, such as glycosylation of produced proteins. However, a problem encountered in eukaryotic cell systems which have been transformed with heterologous genes suitable for the production of protein sequences destined for use, for example, as pharmaceuticals, is that the glycosylation pattern on such proteins often acquires a native pattern, that is, of the eukaryotic cell system in which the protein has been produced: glycosylated proteins are produced that comprise non-animal glycosylation patterns and these in turn may be immunogenic and/or allergenic if applied in animals, including humans.

The use of recombinant glycoproteins produced by higher plants is limited by the plant-specific N-glycosylation that is acquired on such proteins. Compared to mammalian-derived glycoproteins, higher plant-specific glycoproteins contain two additional residues. Moreover, in higher plant glycoproteins terminal beta 1,4-galactose residues are not found, indicating that a beta 1,4-galactosyltransferase is not present in plants. Stable integration and expression of this enzyme in tobacco plants (Bakker et al. (2001) *Proc Natl Acad Sci USA*, 98, 2899-2904) as well as in tobacco BY2 cells (Palacpac et al. (1999) *Proc Natl Acad Sci USA* 96, 4692-4697) has been described. The recombinant human beta 1,4-galactosyltransferase was functional and proteins isolated from transgenic material exhibited terminal beta 1,4-galactose residues. Nevertheless, in higher plants it is not thought possible to suppress the activities of beta 1,2-xylosyltransferase and alpha 1,3-fucosyltransferase, the two enzymes that are considered responsible for transferring the additional, plant-specific residues. These residues are considered to be allergenic for humans (Garcia-Cassado et al. (1996) *Glycobiology* 6, 471-477; van Ree et al. 2000, *J. Biol. Chem.* 275, No. 15, 11451-11458). All data on plant-specific N-glycosylation has been generated in studies with higher plants.

The bryophyte, *Physcomitrella patens*, a haploid non-vascular land plant, can also be used for the production of recombinant proteins (WO 01/25456).

The life cycle of mosses is dominated by photoautotrophic gametophytic generation. The life cycle is completely different to that of the higher plants wherein the sporophyte is the dominant generation and there are notably many differences to be observed between higher plants and mosses.

The gametophyte of mosses is characterised by two distinct developmental stages. The protonema which develops via apical growth, grows into a filamentous network of only two cell types (chloronemal and caulonemal cells). The second stage, called the gametophore, differentiates by caulinary growth from a simple apical system. Both stages are photoautotrophically active. Cultivation of protonema without differentiation into the more complex gametophore has been shown for suspension cultures in flasks as well as for bioreactor cultures (WO 01/25456). Cultivation of fully differentiated and photoautrophically active multicellular tissue containing only a few cell types is not described for higher plants. The genetic stability of the moss cell system provides an important advantage over plant cell cultures and the stability of photoautotrophically active bryophyte cultures has been confirmed (Rieck 1996, Strukturaufklärung und stereochemische Untersuchungen von Sesquiterpenen als Inhaltsstoffe ätherischer Öle. Ph.D. thesis, Hamburg University). In cell cultures of higher plants the secondary metabolism is more differentiated and this results in differences in secondary metabolite profiles.

In addition, there are some important differences between mosses and higher plants on the biochemical level. Sulfate assimilation in *Physcomitrella patens* differs significantly from that in higher plants. The key enzyme of sulfate assimilation in higher plants is adenosine 5'-phosphosulfate reductase. In *Physcomitrella patens* an alternative pathway via phosphoadenosine 5'-phosphosulfate reductase co-exists (Koprivova et al. (2002) J. Biol. Chem. 277, 32195-32201). This pathway has not been characterised in higher plants.

Furthermore, many members of the moss, algae and fern families produce a wide range of polyunsaturated fatty acids (Dembitsky (1993) Prog. Lipid Res. 32, 281-356). For example, arachidonic acid and eicosapentaenoic acid are thought to be produced only by lower plants and not by higher plants. Some enzymes of the metabolism of polyunsaturated fatty acids, (delta 6-acyl-group desaturase) (Girke et al. (1998), *Plant J*, 15, 39-48) and a component of a delta 6 elongase (Zank et al. (2002) *Plant J* 31, 255-268), have been cloned from *Physcomitrella patens*. No corresponding genes have been found in higher plants. This fact appears to confirm that essential differences exist between higher plants and lower plants at the biochemical level.

Further differences are reflected in the regeneration of the cell wall. Protoplasts derived from higher plants regenerate new cell walls in a rapid manner, independently of the culture medium. Direct transfer of DNA via polyethylene glycol (PEG) into protoplasts of higher plants requires pre-incubation at 4 to 10° C. to slow down the process of cell wall regeneration (U.S. Pat. No. 5,508,184). In contrast, cell wall regeneration of protoplasts derived from protonema of *Physcomitrella* is dependent on culture medium. Protoplasts can be cultivated without regeneration of the cell wall over long periods. Without the intention of being bound by theory, it appears that the secretion machinery of the moss protoplast, essential for cell wall regeneration and protein glycosylation, differs from that of higher plants. Moreover, *Physcomitrella patens* shows highly efficient homologous recombination in its nuclear DNA, a unique feature for plants, which enables directed gene disruption (Girke et al. (1998) *Plant J*, 15, 39-48; Strepp et al. (1998) *Proc Natl Acad Sci USA* 95, 4368-4373; Koprivova (2002) J. Biol. Chem. 277, 32195-32201; reviewed by Reski (1999) *Planta* 208, 301-309; Schaefer and Zryd (2001) *Plant Phys* 127, 1430-1438; Schaefer (2002) *Annu. Rev. Plant Biol.* 53, 477-501) further illustrating fundamental differences to higher plants. However, the use of this mechanism for altering glycosylation patterns has proven to be problematic, as shown herein in the examples. Disruption of N-acetylglucosaminyltransferase I (GNT1) in *Physcomitrella patens* resulted in the loss of the specific transcript but only in minor differences of the N-glycosylation pattern. These results were in direct contrast to the loss of Golgi-modified complex glycans in a mutant *Arabidopsis thaliana* plant lacking GNT1 observed by von Schaewen et al. (1993) *Plant Physiol* 102, 1109-1118). Thus, the knockout in *Physcomitrella patens* did not result in the expected modification of the N-glycosylation pattern.

Although the knockout strategy was not successful for GNT1, the present inventors attempted to knock out the beta 1,2-xylosyltransferase (XylT) and alpha 1,3-fucosyltransferase (FucT) in *Physcomitrella patens*. Specific transcripts could not be detected in the resulting plants. Surprisingly, the N-linked glycans isolated from the transgenic plants were found to be modified in the desired manner. No 1,3 linked fucosyl residues could be detected on N-linked glycans of FucT knockout plants and no 1,2 linked xylosyl residues could be detected on N-linked glycans of XylT knockout plants. The isolated transgenic lines showed normal growth which is surprising considering that plant specific glycosylation is highly conserved and therefore would be expected to be significant for function. Double knockouts should therefore have been expected to have had a detrimental effect on the growth of the moss. In addition, compensating were expected but surprisingly were not apparent. Moreover, the double knockout of FucT and XylT resulted in modified N-linked glycans without detectable 1,3 linked fucosyl and 1,2 linked xylosyl residues.

Integration of the human beta 1,4-galactosyltransferase into the genome of a double knockout *Physcomitrella patens* plant resulted in a mammalian-like N-linked glycosylation pattern without the plant specific fucosyl and xylosyl residues and with mammalian-like terminal 1,4 galactosyl residues. The galactosyltransferase was found to be active. Such a modification of N-linked glycans without loss of viability was not expected because N-glycosylation is very complex and well regulated. It is not only dependent on developmental stages (for plants: Elbers et al. (2001) *Plant Phys* 126, 1314-1322) but also dependent on culture conditions (for mammalian cell culture: Hills et al. (2001) Biotechnol. Bioeng. 75, 239-251).

It is an object of the present invention to provide a more efficient method of producing animal proteins comprising animal glycosylation patterns, and in particular, glycosylated human proteins comprising human glycosylation patterns thereon. It is a further object to provide an efficient process for the production of heterologous animal proteins comprising animal glycosylation patterns, particularly human proteins comprising human glycosylation patterns in bryophytes, such as *Physcomitrella patens*.

These and other objects will become apparent from the following description and examples provided herein.

DETAILED DESCRIPTION

According to the present invention there is provided a transformed bryophyte cell that comprises i) a dysfunctional fucosyl transferase nucleotide sequence and ii) a dysfunctional xylosyl transferase nucleotide sequence.

The bryophyte cell of the invention is one from a moss selected from the group mosses including liverworts., of species from the genera *Physcomitrella, Funaria, Sphagnum, Ceratodon, Marchantia* and *Sphaerocarpos*. The bryophyte cell is preferably from *Physcomitrella patens*.

The bryophyte cell, such as a *Physcomitrella patens* cell, can be any cell suitable for transformation according to methods of the invention as described herein, and may be a moss protoplast cell, a cell found in protonema tissue or other cell type. Indeed, the skilled addressee will appreciate that moss plant tissue comprising populations of transformed bryophyte cells according to the invention, such as transformed protonemal tissue also forms an aspect of the present invention.

"Dysfunctional" as used herein means that the nominated trans-ferrase nucleotide sequences of fucosyl transferase (fucT) and xylosyl transferase (xylT) are substantially incapable of encoding mRNA that codes for functional fucT and xylT proteins that are capable of modifying plant N-linked glycans with plant-like glycosylation patterns comprising 1,3 linked fucosyl and 1,2 linked xylosyl residues. In a preferment, the dysfunctional fucT and xylT plant transferase nucleotide sequences comprise targeted insertions of exogenous nucleotide sequences into endogenous, that is genomic, native fucT and xylT genes comprised in the nuclear bryophyte genome (whether it is a truly native bryophyte genome, that is in bryophyte cells that have not been transformed previously by man with other nucleic acid sequences, or in a transformed nuclear bryophyte genome in which nucleic acid sequence insertions have been made previously of desired nucleic acid sequences) which substantially inhibits or represses the transcription of mRNA coding for functional fucT and xylT transferase activity.

In a further preferment, the dysfunctional fucT and xylT plant transferase nucleotide sequences may comprise targeted deletions of the whole or substantially the whole endogenous gene sequences thereof, or indeed, targeted partial deletions of the endogenous gene sequences of fucT and xylT nucleotide sequences, thus rendering such sequences dysfunctional within the context of the invention.

Bryophyte cells of the invention or ancestors thereof may be any which have been transformed previously with heterologous genes of interest that code for primary sequences of proteins of interest which are glycosylated with mammalian glycosylation patterns as described herein. Preferably, the glycosylation patterns are of the human type. Alternatively, the bryophyte cell may be transformed severally, that is, simultaneously or over time with nucleotide sequences coding for at least a primary protein sequence of interest, typically at least a pharmaceutical protein of interest for use in humans or mammals such as livestock species including bovine, ovine, equine and porcine species, that require mammalian glycosylation patterns to be placed on them in accordance with the methods of the invention as described herein. Such pharmaceutical glycoproteins for use in mammals, including man include but are not limited to proteins such as insulin, preproinsulin, VEGF, proinsulin, glucagon, interferons such as alpha-interferon, beta-interferon, gamma-interferon, blood-clotting factors selected from Factor VII, VIII, IX, X, XI, and XII, fertility hormones including luteinising hormone, follicle stimulating hormone growth factors including epidermal growth factor, platelet-derived growth factor, granulocyte colony stimulating factor and the like, prolactin, oxytocin, thyroid stimulating hormone, adrenocorticotropic hormone, calcitonin, parathyroid hormone, somatostatin, erythropoietin (EPO), enzymes such as beta-glucocerebrosidase, haemoglobin, serum albumin, collagen, fusion proteins such as the fusion protein of TNF alpha receptor ligand binding domain with Fc portion of IgG and the like. Furthermore, the method of the invention can be used for the production of antibodies such as specific monoclonal antibodies or active fragments thereof.

In a preferment, there is provided a transformed bryophyte cell that comprises i) a dysfunctional fucosyl transferase nucleotide sequence and ii) a dysfunctional xylosyl transferase nucleotide sequence and iii) a nucleotide sequence operably linked to an exogenous promoter that drives expression in the said bryophyte cell wherein said nucleotide sequence encodes a functional mammalian galactosyl transferase that is expressed in the bryophyte cell.

In a further preferment, the mammalian galactosyl transferase nucleotide sequence is a beta-1,4 galactosyl transferase (beta-1,4 galT) and most preferably is a human beta-1,4 galactosyl transferase nucleotide sequence. The skilled addressee will appreciate that the beta-1,4 galT nucleotide sequence may be a cDNA sequence or a genomic DNA sequence and may comprise a degeneratively equivalent nucleotide beta-1,4 galT sequence as long as the N-glycan glycosylation pattern on any desired glycosylated exogenous protein produced in the transformed bryophyte cells or bryophyte tissue of the invention is substantially mammalian in pattern, if not completely mammalian in pattern, and most preferably, where appropriate, is human in pattern.

Detailed information on the culturing of mosses which are suitable for use in the invention, such as *Leptobryum pyriforme* and *Sphagnum magellanicum* in bioreactors, is known in the prior art (see, for example, E. Wilbert, "Biotechnological studies concerning the mass culture of mosses with particular consideration of the arachidonic acid metabolism", Ph.D. thesis, University of Mainz (1991); H. Rudolph and S. Rasmussen, Studies on secondary metabolism of Sphagnum cultivated in bioreactors, Crypt. Bot., 3, pp. 67-73 (1992)). Especially preferred for the purposes of the present invention is the use of *Physcomitrella patens*, since molecular biology techniques are practised on this organism (for a review see R. Reski, Development, genetics and molecular biology of mosses, Bot. Acta, 111, pp. 1-15 (1998)).

Suitable transformation systems have been developed for the biotechnological exploitation of *Physcomitrella* for the production of heterologous proteins. For example, successful transformations have been carried out by direct DNA transfer into protonema tissue using particle guns. PEG-mediated DNA transfer into moss protoplasts has also been successfully achieved. The PEG-mediated transformation method has been described many times for *Physcomitrella patens* and leads both to transient and to stable transformants (see, for example, K. Reutter and R. Reski, Production of a heterologous protein in bioreactor cultures of fully differentiated moss plants, Pl. Tissue culture and Biotech., 2, pp. 142-147 (1996)).

In a further embodiment of the present invention there is provided a method of producing at least a bryophyte cell wherein fucT and xylT activity is substantially reduced that comprises introducing into the said cell i) a first nucleic acid sequence that is specifically targeted to an endogenous fucosyl transferase nucleotide sequence and ii) a second nucleic acid sequence that is specifically targeted to an endogenous xylosyl transferase nucleotide sequence.

The skilled addressee will appreciate that the order of introduction of said first and second transferase nucleic acid sequences into the bryophyte cell is not important: it can be performed in any order. The first and second nucleic acid sequences can be targeted to specific portions of the endogenous, native fucT and xylT genes located in the nuclear genome of the bryophyte cell defined by specific restriction enzyme sites thereof, for example, according to the examples as provided herein. By specifically targeting the sequences of the native fucT and xylT transferase genes with nucleotide sequences that specifically integrate with the target native transferase genes of interest, the expression of the said sequences is substantially impaired if not completely disrupted.

In a preferred embodiment of the present invention there is provided a method of producing at least a heterologous or exogenous glycosylated mammalian protein in a transformed bryophyte cell that comprises:
i) introducing into said cell a first isolated nucleic acid that comprises a first nucleic acid sequence that is specifically targeted to an endogenous fucosyl transferase nucleotide sequence; and
ii) introducing into said cell a second nucleic acid sequence that is specifically targeted to an endogenous xylosyl transferase nucleotide sequence; and
iii) introducing into said cell a third isolated nucleic acid sequence that comprises nucleic acid operably linked to an exogenous promoter that drives expression in a bryophyte cell wherein said nucleic acid encodes at least one mammalian galactosyl transferase polypeptide.

In this embodiment of the invention the at least one mammalian galactosyl transferase polypeptide is preferably a beta-1,4, galactosyl transferase (beta-1,4 galT) and most preferably is a human beta-1,4 galactosyl transferase nucleotide sequence.

Preferably all glycosylated mammalian proteins mentioned herein-above are of the human type. Other proteins that are contemplated for production in the present invention include proteins for use in veterinary care and may correspond to animal homologues of the human proteins mentioned herein.

An exogenous promoter is one that denotes a promoter that is introduced in front of a nucleic acid sequence of interest and is operably associated therewith. Thus an exogenous promoter is one that has been placed in front of a selected nucleic acid component as herein defined and does not consist of the natural or native promoter usually associated with the nucleic acid component of interest as found in wild type circumstances. Thus a promoter may be native to a bryophyte cell of interest but may not be operably associated with the nucleic acid of interest in front in wild-type bryophyte cells. Typically, an exogenous promoter is one that is transferred to a host bryophyte cell from a source other than the host cell.

The cDNA's encoding the galT proteins, the glycosylated and the mammalian proteins as described herein contain at least one type of promoter that is operable in a bryophyte cell, for example, an inducible or a constitutive promoter operatively linked to a galT nucleic acid sequence and/or second nucleic acid sequence for a glycosylated mammalian protein as herein defined and as provided by the present invention. As discussed, this enables control of expression of the gene(s).

The term "inducible" as applied to a promoter is well understood by those skilled in the art. In essence, expression under the control of an inducible promoter is "switched on" or increased in response to an applied stimulus (which may be generated within a cell or provided exogenously). The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus. The preferable situation is where the level of expression increases upon application of the relevant stimulus by an amount effective to alter a phenotypic characteristic. Thus an inducible (or "switchable") promoter may be used which causes a basic level of expression in the absence of the stimulus which level is too low to bring about a desired phenotype (and may in fact be zero). Upon application of the stimulus, expression is increased (or switched on) to a level, which brings about the desired phenotype.

As alluded to herein, bryophyte expression systems are also known to the man skilled in the art. A bryophyte promoter, in particular a *Physcomitrella patens* promoter, is any DNA sequence capable of binding a host DNA-dependent RNA polymerase and initiating the downstream (3') transcription of a coding sequence (e.g. structural gene) into mRNA. A promoter will have a transcription initiation region which is usually placed proximal to the 5' end of the coding sequence. This transcription initiation region usually includes an RNA polymerase binding site (the "TATA Box") and a transcription initiation site. A bryophyte promoter may also have a second domain called an upstream activator sequence (UAS), which, if present, is usually distal to the structural gene. The UAS permits regulated (inducible) expression. Constitutive expression occurs in the absence of a UAS. Regulated expression may be either positive or negative, thereby either enhancing or reducing transcription.

The skilled addressee will appreciate that bryophyte promoter sequences encoding enzymes in bryophyte metabolic pathways can provide particularly useful promoter sequences.

In addition, synthetic promoters which do not occur in nature may also function as bryophyte promoters. For example, UAS sequences of one bryophyte promoter may be joined with the transcription activation region of another bryophyte promoter, creating a synthetic hybrid promoter. An example of a suitable promoter is the one used in the TOP 10 expression system for *Physcomitrella patens* by Zeidler et al. (1996) Plant. Mol. Biol. 30, 199-205). Furthermore, a bryophyte promoter can include naturally occurring promoters of non-bryophyte origin that have the ability to bind a bryophyte DNA-dependent RNA polymerase and initiate transcription. Examples of such promoters include those described, inter alia, the rice P-Actin 1 promoter and the *Chlamydomonas* RbcS promoter (Zeidler et al. (1999) J. Plant Physiol. 154, 641-650), Cohen et al., Proc. Natl. Acad. Sci. USA, 77: 1078, 1980; Henikoff et al., Nature, 283: 835, 1981; Hollenberg et al., Curr. Topics Microbiol. Immunol., 96: 119, 1981; Hollenberg et al., "The Expression of Bacterial Anti-biotic Resistance Genes in the Yeast *Saccharomyces cerevisiae*", in: Plasmids of Medical, Environmental and Commercial Importance (eds. K. N. Timms and A. Puhler), 1979; Mercerau-Puigalon et al., Gene, 11: 163, 1980; Panthier et al., Curr. Genet., 2: 109, 1980.

A DNA molecule may be expressed intracellularly in bryophytes. A promoter sequence may be directly linked with the DNA molecule, in which case the first amino acid at the N-terminus of the recombinant protein will always be a methionine, which is encoded by the AUG start codon on the mRNA. If desired, methionine at the N-terminus may be cleaved from the protein by in vitro incubation with cyanogen bromide.

Alternatively, foreign proteins can also be secreted from the bryophyte cell into the growth media by creating chimeric DNA molecules that encode a fusion protein comprised of a leader sequence fragment that provides for secretion in or out of bryophyte cells of the foreign protein. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell.

DNA encoding suitable signal sequences can be derived from genes for secreted bryophyte proteins, such as leaders of non-bryophyte origin, such as a VEGF leader, exist that may also provide for secretion in bryophyte cells.

Transcription termination sequences that are recognized by and functional in bryophyte cells are regulatory regions located 3' to the translation stop codon, and thus together with the promoter flank the coding sequence. These sequences direct the transcription of an mRNA which can be translated into the polypeptide encoded by the DNA. An example of a suitable termination sequence that works in *Physcomitrella patens* is the termination region of Cauliflower mosaic virus.

Typically, the components, comprising a promoter, leader (if desired), coding sequence of interest, and transcription termination sequence, are put together into expression constructs of the invention. Expression constructs are often maintained in a DNA plasmid, which is an extrachromosomal element capable of stable maintenance in a host, such as a bacterium. The DNA plasmid may have two origins of replication, thus allowing it to be maintained, for example, in a bryophyte for expression and in a prokaryotic host for cloning and amplification. Generally speaking it is sufficient if the plasmid has one origin of replication for cloning and amplification in a prokaryotic host cell. In addition, a DNA plasmid may be either a high or low copy number plasmid. A high copy number plasmid will generally have a copy number ranging from about 5 to about 200, and usually about 10 to about 150. A host containing a high copy number plasmid will preferably have at least about 10, and more preferably at least about 20. Either a high or low copy number vector may be selected, depending upon the effect of the vector and the foreign protein on the host (see, e.g., Brake et al., supra).

Alternatively, the expression constructs can be integrated into the bryophyte genome with an integrating vector. Integrating vectors usually contain at least one sequence homologous to a bryophyte chromosome that allows the vector to integrate, and preferably contain two homologous sequences flanking the expression construct. An integrating vector may be directed to a specific locus in moss by selecting the appropriate homologous sequence for inclusion in the vector as described and exemplified herein. One or more expression constructs may integrate. The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct.

Usually, extrachromosomal and integrating expression constructs may contain selectable markers to allow for the selection of bryophyte cells that have been transformed.

Selectable markers may include biosynthetic genes that can be expressed in the moss host, such as the G418 or hygromycin B resistance genes, which confer resistance in bryophyte cells to G418 and hygromycin B, respectively. In addition, a suitable selectable marker may also provide bryophyte cells with the ability to grow in the presence of toxic compounds, such as metal.

Alternatively, some of the above-described components can be put together into transformation vectors. Transformation vectors are usually comprised of a selectable marker that is either maintained in a DNA plasmid or developed into an integrating vector, as described above.

Methods of introducing exogenous DNA into bryophyte cells are well-known in the art, and are described inter alia by Schaefer D. G. "Principles and protocols for the moss *Physcomitrella patens*", (May 2001) Institute of Ecology, Laboratory of Plant Cell Genetics, University of Lausanne Didier.Schaefer@ie-pc.unil.ch; Reutter K. and Reski R., Plant Tissue Culture and Biotechnology September 1996, Vol. 2, No. 3; Zeidler M et al., (1996), Plant Molecular Biology 30:199-205.

Those skilled in the art are well able to construct vectors and design protocols for recombinant nucleic acid sequence or gene expression as described above. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology*, Second Edition, Ausubel et al. eds., John Wiley & Sons, 1992. The disclosures of Sambrook et al. and Ausubel et al. are incorporated herein by reference.

Naturally, the skilled addressee will appreciate that each nucleic acid sequence coding for the appropriate galT and polypeptide to be glycosylated will be under regulatory control of its own exogenous promoter and terminator. When two or more target proteins are destined to be produced from a single carrier RNA it is preferable if they are able to be readily separated, for example by binding to different protein-specific antibodies (monoclonal or polyclonal) in the harvesting phase of the bryophyte cell culture system.

As described above, selectable genetic markers may facilitate the selection of transgenic bryophyte cells and these may consist of chimeric genes that confer selectable phenotypes as alluded to herein.

When introducing selected glycosyl transferase nucleic acid sequences and polypeptide sequences for glycosylation into a bryophyte cell, certain considerations must be taken into account, well known to those skilled in the art. The nucleic acid(s) to be inserted should be assembled within a construct, which contains effective regulatory elements, which will drive transcription. There must be available a method of transporting the construct into the cell. Once the construct is within the cell membrane, integration into the endogenous chromosomal material either will or will not occur.

The invention further encompasses a host cell transformed with vectors or constructs as set forth above, especially a bryophyte or a microbial cell. Thus, a host cell, such as a bryophyte cell, including nucleotide sequences of the invention as herein indicated is provided. Within the cell, the nucleotide sequence may be incorporated within the chromosome.

Also according to the invention there is provided a bryophyte cell having incorporated into its genome at least a nucleotide sequence, particularly heterologous nucleotide sequences, as provided by the present invention under operative control of regulatory sequences for control of expression as herein described. The coding sequence may be operably linked to one or more regulatory sequences which may be heterologous or foreign to the nucleic acid sequences employed in the invention, such as not naturally associated with the nucleic acid sequence(s) for its (their) expression. The nucleotide sequence according to the invention may be placed under the control of an externally inducible promoter to place expression under the control of the user. A further aspect of the present invention provides a method of making such a bryophyte cell, particularly a *Physcomitrella patens* cell involving introduction of nucleic acid sequence(s) contemplated for use in the invention or at least a suitable vector including the sequence(s) contemplated for use in the invention into a bryophyte cell and causing or allowing recombination between the vector and the bryophyte cell genome to introduce the said sequences into the genome. The invention extends to bryophyte cells, particularly *Physcomitrella patens* cells containing a GalT nucleotide and/or a nucleotide sequence coding for a polypeptide sequence destined for the addition of a mammalian glycosylation pattern thereto and suitable for use in the invention as a result of introduction of the nucleotide sequence into an ancestor cell.

The term "heterologous" may be used to indicate that the gene/sequence of nucleotides in question have been introduced into bryophyte cells or an ancestor thereof, using genetic engineering, ie by human intervention. A transgenic bryophyte cell, i.e. transgenic for the nucleotide sequence in question, may be provided. The transgene may be on an extra-genomic vector or incorporated, preferably stably, into the genome. A heterologous gene may replace an endogenous equivalent gene, ie one that normally performs the same or a similar function, or the inserted sequence may be additional to the endogenous gene or other sequence. An advantage of introduction of a heterologous gene is the ability to place expression of a sequence under the control of a promoter of choice, in order to be able to influence expression according to preference. Nucleotide sequences heterologous, or exogenous or foreign, to a bryophyte cell may be non-naturally occurring in cells of that type, strain or species. Thus, a nucleotide sequence may include a coding sequence of or derived from a particular type of bryophyte cell, such as a *Physcomitrella patens* cell, placed within the context of a bryophyte cell of a different type or species. A further possibility is for a nucleotide sequence to be placed within a bryophyte cell in which it or a homologue is found naturally, but wherein the nucleotide sequence is linked and/or adjacent to nucleic acid which does not occur naturally within the cell, or cells of that type or species or strain, such as operably linked to one or more regulatory sequences, such as a promoter sequence, for control of expression. A sequence within a bryophyte or other host cell may be identifiably heterologous, exogenous or foreign.

The present invention also encompasses the desired polypeptide expression product of the combination of nucleic acid molecules according to the invention as disclosed herein or obtainable in accordance with the information and suggestions herein. Also provided are methods of making such an expression product by expression from nucleotide sequences encoding therefore under suitable conditions in suitable host cells e.g. E. coli. Those skilled in the art are well able to construct vectors and design protocols and systems for expression and recovery of products of recombinant gene expression.

A polypeptide according to the present invention may be an allele, variant, fragment, derivative, mutant or homologue of the (a) polypeptides as mentioned herein. The allele, variant, fragment, derivative, mutant or homologue may have substantially the same function of the polypeptides alluded to above and as shown herein or may be a functional mutant thereof. In the context of pharmaceutical proteins as described herein for use in humans, the skilled addressee will appreciate that the primary sequence of such proteins and their glycosylation pattern will mimic or preferably be identical to that found in humans.

"Homology" in relation to an amino acid sequence of the invention may be used to refer to identity or similarity, preferably identity. As noted already above, high level of amino acid identity may be limited to functionally significant domains or regions, e.g. any of the domains identified herein.

In particular, homologues of the particular bryophyte-derived polypeptide sequences provided herein, are provided by the present invention, as are mutants, variants, fragments and derivatives of such homologues. Such homologues are readily obtainable by use of the disclosures made herein. Naturally, the skilled addressee will appreciate that homologues of the glycosylated protein sequences per se, other than those homologues that due to the degeneracy of the genetic code give rise to amino acid sequences that are true copies (i.e. 100% identical) of the mammalian proteins of interest, and especially of human proteins of interest, are encompassed within the present invention. Thus the present invention also extends to polypeptides which include amino acid sequences with GalT function as defined herein and as obtainable using sequence information as provided herein. The GalT homologues may at the amino acid level have homology, that is identity, with the amino acid sequences described in the prior art as described herein i.e. under the database accession numbers provided in the examples section, preferably at least about 50%, or at least 55%, or at least about 60%, or at least about 65%, or at least about 70%, or at least about 75%, or at least about 80% homology, or at least about 85%, or at least about 88% homology, or at least about 90% homology and most preferably at least about 95% or greater homology provided that such proteins have a GalT activity that fits within the context of the present invention.

In certain embodiments, an allele, variant, derivative, mutant derivative, mutant or homologue of the specific sequence may show little overall homology, say about 20%, or about 25%, or about 30%, or about 35%, or about 40% or about 45%, with the specific sequence. However, in functionally significant domains or regions, the amino acid homology may be much higher. Putative functionally significant domains or regions can be identified using processes of bioinformatics, including comparison of the sequences of homologues.

Functionally significant domains or regions of different polypeptides may be combined for expression from encoding nucleic acid as a fusion protein. For example, particularly advantageous or desirable properties of different homologues may be combined in a hybrid protein, such that the resultant expression product, with GalT function, may include fragments of various parent proteins, if appropriate.

Similarity of amino acid sequences may be as defined and determined by the TBLASTN program, of Altschul et al. (1990) *J. Mol. Biol.* 215: 403-10, which is in standard use in the art. In particular, TBLASTN 2.0 may be used with Matrix BLOSUM62 and GAP penalties: existence: 11, extension: 1. Another standard program that may be used is BestFit, which is part of the Wisconsin Package, Version 8, September 1994, (Genetics Computer Group, 575 Science Drive, Madison, Wis.; USA, Wisconsin 53711). BestFit makes an optimal alignment of the best segment of similarity between two sequences. Optimal alignments are found by inserting gaps to maximize the number of matches using the local homology algorithm of Smith and Waterman (*Adv. Appl. Math.* (1981) 2: 482-489). Other algorithms include GAP, which uses the Needleman and Wunsch algorithm to align two complete sequences that maximizes the number of matches and minimizes the number of gaps. As with any algorithm, generally the default parameters are used, which for GAP are a gap creation penalty=12 and gap extension penalty=4. Alternatively, a gap creation penalty of 3 and gap extension penalty of 0.1 may be used. The algorithm FASTA (which uses the method of Pearson and Lipman (1988) *PNAS USA* 85: 2444-2448) is a further alternative.

Use of either of the terms "homology" and "homologous" herein does not imply any necessary evolutionary relationship between compared sequences, in keeping for example with standard use of terms such as "homologous recombination" which merely requires that two nucleotide sequences are sufficiently similar to recombine under the appropriate conditions.

It is to be understood that the teaching of all references cited herein is incorporated into the teaching of the specification.

EXAMPLES

Methods and Materials

Plant Material

The wild-type strain of *Physcomitrella patens* (Hedw.) B. S. G. characterised by Reski et al. (1994) Genome analysis of the moss *Physcomitrella patens* (Hedw.) B. S. G. *Mol Gen Genet.* 244, 352-359) was used. It is a subculture of strain 16/14 which was collected by H. L. K. Whitehouse in Gransden Wood, Huntingdonshire, UK and was propagated by Engel (1968) *Am J Bot* 55, 438-446.).

Construction of pRT101VEGF C3

Human vascular endothelial growth factor 121 ($VEGF_{121}$) cDNA without leader sequence was excised as an NdeI-SalI fragment from pCYTEXP-$VEGF_{121}$ (available from GBF, Braunschweig, Germany). This fragment was blunt-ended by the Klenow reaction and introduced into pRT101 (Töpfer et al. (1987) *NAR* 15, 589) at the SmaI restriction site to form plasmid pRT101VEGF C3. In this construct, the $VEGF_{121}$ cDNA without leader sequence was placed downstream of the CaMV 35 S promoter and terminated by the CaMV terminator (Gorr (1999) Biotechnologische Nutzung von *Physcomitrella patens* (Hedw.) B. S. G. Ph.D. thesis, Hamburg University).

Construction of pRT101TPVEGF C3

The sequence for VEGF signal peptide (sorting signal for secretion) was cloned into pRT101VEGF C3. The signal peptide cDNA was amplified from the plasmid pRT101 P21 (Gorr (1999), supra) using the 5' primer MoB323 5'-ATA CTC GAG GAA GAT GAA CTT TTC TGC CTG TCT TGG-3' (SEQ ID NO 1) containing an XhoI restriction side and 3' primer MoB349 5'-CTG CCA TGG GTG CAG CCT GGG ACC AC-3' (SEQ ID NO 2) containing a NcoI restriction side. The amplified DNA was digested with XhoI and NcoI and ligated into pRT101VEGF C3 (XhoI/NcoI digested) resulting in pRT101TPVEGF C3. The resulting plasmid contained the coding sequences for the VEGF signal peptide and $VEGF_{121}$ in frame under the control of the CaMV 35 S promoter.

Standard Culture Conditions

Plants were grown axenicallly under sterile conditions in plain inorganic liquid modified Knop medium (1000 mg/l $Ca(NO_3)_2 \times 4H_2O$ 250 mg/l KCl, 250 mg/l $KH_2PO_4$, 250 mg/l $MgSO_4 \times 7H_2O$ and 12.5 mg/l $FeSO_4 \times 7H_2O$; pH 5.8 (Reski and Abel (1985) *Planta* 165, 354-358). Plants were grown in 500 ml Erlenmeyer flasks containing 200 ml of culture medium and flasks were shaken on a Certomat R shaker (B. Braun Biotech International, Germany) set at 120 rpm. Conditions in the growth chamber were 25+/−3° C. and a light-dark regime of 16:8 h. The flasks were illuminated from above by two fluorescent tubes (Osram L 58 W/25) providing 35 micromols$^{-1}$m$^{-2}$. The cultures were subcultured once a week by disintegration using an Ultra-Turrax homogenizer (IKA, Staufen, Germany) and inoculation of two new 500 ml Erlenmeyer flasks containing 100 ml fresh Knop medium.

Protoplast Isolation

After filtration the moss protonemata were preincubated in 0.5 M mannitol. After 30 min, 4% Driselase (Sigma, Deisenhofen, Germany) was added to the suspension. Driselase was dissolved in 0.5 M mannitol (pH 5.6-5.8), centrifuged at 3600 rpm for 10 min and sterilised by passage through a 0.22 microm filter (Millex GP, Millipore Corporation, USA). The suspension, containing 1% Driselase (final concentration), was incubated in the dark at RT and agitated gently (best yields of protoplasts were achieved after 2 hours of incubation) (Schaefer, "Principles and protocols for the moss *Physcomitrella patens*", (May 2001) Institute of Ecology, Laboratory of Plant Cell Genetics, University of Lausanne Didier.Schaefer@ie-pc.unil.ch). The suspension was passed through sieves (Wilson, C L F, Germany) with pore sizes of 100 microm and 50 microm. The suspension was centrifuged in sterile centrifuge tubes and protoplasts were sedimented at RT for 10 min at 55 g (acceleration of 3; slow down at 3; Multifuge 3 S-R, Kendro, Germany) (Schaefer, supra). Protoplasts were gently resuspended in W5 medium (125 mM $CaCl_2 \times 2H_2O$; 137 mM NaCl; 5.5 mM glucose; 10 mM KCl; pH 5.6; 660-680 mOsm; sterile filtered). The suspension was centrifuged again at RT for 10 min at 55 g (acceleration of 3; slow down at 3; Multifuge 3 S-R, Kendro, Germany). Protoplasts were gently resuspended in W5 medium (Rother et al. (1994) *J Plant Physiol* 143, 72-77). For counting protoplasts a small volume of the suspension was transferred to a Fuchs-Rosenthal-chamber.

Transformation Protocol

For transformation protoplasts were incubated on ice in the dark for 30 minutes. Subsequently, protoplasts were sedimented by centrifugation at RT for 10 min at 55 g (acceleration of 3; slow down at 3; Multifuge 3 S-R, Kendro). Protoplasts were resuspended in 3M medium (15 mM $CaCl_2 \times 2H_2O$; 0.1% MES; 0.48 M mannitol; pH 5.6; 540 mOsm; sterile filtered, Schaefer et al. (1991) *Mol Gen Genet.* 226, 418-424) at a concentration of $1.2 \times 10^6$ protoplasts/ml (Reutter and Reski (1996) Production of a heterologous protein in bioreactor cultures of fully differentiated moss plants, Pl. Tissue culture and Biotech., 2 pp. 142-147). 250 microliter of this protoplast suspension were dispensed into a new sterile centrifuge tube, 50 microliter DNA solution (column purified DNA in $H_2O$ (Qiagen, Hilden, Germany); 10-100 microliter; optimal DNA amount of 60 microgram) was added and finally 250 microliter PEG-solution (40% PEG 4000; 0.4 M mannitol; 0.1 M $Ca(NO_3)_2$; pH 6 after autoclaving) was added. The suspension was immediately but gently mixed and then incubated for 6 min at RT with occasional gentle mixing. The suspension was diluted progressively by adding 1, 2, 3 and 4 ml of 3M medium. The suspension was centrifuged at 20° C. for 10 minutes at 55 g (acceleration of 3; slow down at 3; Multifuge 3 S-R, Kendro).

The pellet was re-suspended a) for transient transformation experiments in 300 microliter or 400 microliter 3M medium. Cultivation of transformed protoplasts was performed in 96 well plates (300 microliter, Nunclon, Nunc GmbH, Wiesbaden, Germany) or 48 well plates (400 microliter, Cellstar, greiner bio-one, Frickenhausen, Germany);

b) for stable transformation in 3 ml regeneration medium (modified Knop medium; 5% glucose; 3% mannitol; 540 mOsm; pH 5.6-5.8). Regeneration and selection was performed as described by Strepp et al. (1998) *Proc Natl Acad Sci USA* 95, 4368-4373). For selection Knop's media were supplemented either with 50 microgram/ml G418 or with 30 microgram/ml Hygromycin B.

Co-transformation was performed by transferring 10 microgram undigested pRT99 (Topfer et al. (1988) Versatile cloning vectors for transient gene expression and direct gene transfer in plant cells. NAR 16, 8725) containing the npt II gene as a selection marker in parallel with 10 microgram linearised DNA of each knockout and/or integration construct into the protoplasts.

MALDI-T of MS of Moss Glycans

Plant material was cultivated in liquid culture, isolated by filtration, frozen in liquid nitrogen and stored at −80° C. Protein bands were excised from Coomassie-stained SDS-polyacrylamide gels. The material was shipped under dry ice. The MALDI-TOF MS analyses were done in the laboratory of Prof. Dr. F. Altmann, Glycobiology Division, Institut für Chemie, Universität für Bodenkultur, Vienna, Austria.

0.2 to 9 g fresh weight of *Physcomitrella patens* was digested with pepsin. N-glycans were obtained from the digest as described by Wilson et al. (2001). Essentially, the glycans were released by treatment with peptide:N-glycosidase A and analysed by MALDI-TOF mass spectrometry on a DYNAMO (Thermo BioAnalysis, Santa Fe, N. Mex.).

Synthesis of Oligonucleotides

For design of synthetic oligonucleotides the standard code for nucleotides was used. For design of degenerated primers the standard code was used:

R=A,G; Y=T,C; W=A,T; S=C,G; M=A,C; K=G,T; H=A,T,C; B=G,C,T; V=G,A,C; D=G,A,T; N=G,A,C,T

Examples

1. Cloning of the 1,2-N-acetylglucosaminyltransferase I from *Physcomitrella patens* and Analysis of the Knockout Plants 1.1 Cloning of the cDNA and Genomic DNA for GNTI A fragment of the cDNA for the GNTI was obtained by performing two rounds of PCR with degenerated primers on the cDNA from *P. patens* WT. These primers were created on the basis of a protein alignment of the known GNTIs from plants. In the first round primers GNT(d)1 (5'-GTNGCNGC-NGTNGTNGTNATGGC-3', SEQ ID NO 3) and GTN(d)₃ (5'-CCYTTRTANGCNGCNC(TG)NGGNACNCC-3', SEQ ID NO 4) were used and then the product from this PCR was subjected to subsequent PCR with the primers GTN(d)₂ (5'-TAYAARATN(CA)GNCAYTAYAARTGG-3', SEQ ID NO 5) and GTN(d)₄ (5'-ARRTAYTGYTTRAARAAYTGNCC-3', SEQ ID NO 6). The PCR resulted in a 500 bp product which was cloned into pCR 4 TOPO and sequenced from both ends.

To obtain the missing 5'-end of the cDNA 5' RACE was performed with the primers: 5RACEG3 (5'-GTCCGTGTC-CAATAAAGGAG-3', SEQ ID NO 7), 5RACEG4 (5'-GTCGGGAGAGATTTCCATGTC-3', SEQ ID NO 8), 5RACEG5 (5'-CTAAGATGACGACCCTTCGG-3', SEQ ID NO 9) which gave an additional 300 bp fragment of cDNA, however still without the initial Met. Therefore, on the basis of the new sequence another round of 5' RACE was performed with the primers: 5RACE6 (5'-CATCCTGAGAAA-CAAAAAGTGG-3', SEQ ID NO 10), 5RACE7 (5'-AGTTA-CAGACTTCAATGTACG-3', SEQ ID NO 11), and 5RACE8 (5'-AATCAGGACGGTTGCAAGCC-3', SEQ ID NO 12) which gave an additional 400 bp fragment containing the initiation codon.

To obtain the missing 3'-end of the cDNA 3' RACE was performed correspondingly with the primers: 3RACEG1 (5'-TTATCCGACCTGAAGTTTGC-3', SEQ ID NO 13), 3RACEG2 (5'-GACCTACAATTTTGGAGAGC-3', SEQ ID NO 14) which resulted in a fragment about 450 bp with the stop codon and finally the complete 1416 bp of the cDNA for GNTI (GenBank: AJ429143).

The corresponding 5788 bp of the genomic sequence was obtained by cloning the GNTI gene in three pieces by PCR on WT *P. patens* genomic DNA with the specific primers: GNT5F (5'-TGGGCTTTAACACAACTTTT-3', SEQ ID NO 15) and GTN6R (5'-GCCCTAAGCTTGATCCCTG-3', SEQ ID NO 16), GNT21F (5'-ATGGCAGATATGGCTCGATTG-3', SEQ ID NO 17) and 5RACEG5 (5'-CTAAGATGACGAC-CCTTCGG-3', SEQ ID NO 9), 3RACEG1 (5'-TTATC-CGACCTGAAGTTTGC-3', SEQ ID NO 13) and GNT15R (5'-AGTTTCTATGGTATCTAACTGC-3', SEQ ID NO 18) which were sequenced by primer walking.

1.2 Creating the Knockout Construct for GNTI

To generate the knockout construct two fragments were synthesized by PCR on the genomic DNA with the primers for the 5'-end of the construct: GNTHT7 (5'-GAGCATC-CAAGCTTGACCTGG-3', SEQ ID NO 19) and GNTET7 (5'-GCACCGTGAATTCTTCTAGCTT-3', SEQ ID NO 20) and for the 3'-end correspondingly GNTHT3 (5'-GGAA-GAACAAGCTTCAAAGTGGC-3', SEQ ID NO 21) and GNTPT3 (5'-GATCCCTGCAGATCTCAAACG-3', SEQ ID NO 22). The thus obtained fragments of 469 bp and 835 bp of genomic DNA were first cloned into the TOPO-PCR plasmid (Invitrogen, USA). The fragments were then cut out from this vector with EcoRI/HindIII and PstI/HindIII, respectively and cloned into the PCRII vector digested with EcoRI and PstI. The resulting plasmid was digested with HindIII and the nptII selection cassette was introduced, which was obtained by digestion with the same restriction enzyme from the vector pRT101neo (Girke et al. 1998).

For the transformation the knockout plasmid was digested with EcoRI and BcuI restriction enzymes and 30 microgram were used for the transformation.

1.3 Pre-Screening of the Transgenic Plants

For the pre-screening of the resistant plants, small pieces of gametophores (1-5 mg) were treated for 30 min at 45° C. in 75 mM Tri-HCl, pH 8, containing 20 mM $(NH_4)_2SO_4$ and 0.1% Tween 20, and 3 microliter of this extract was used for PCR with the following four pairs of primers: GNT7F (5'-GTTC-SATGGTTTGAGCAGG-3', SEQ ID NO 23) and GNT8R (5'-GCGACCTTTCCTATTCTCC-3', SEQ ID NO 24) to detect a disruption of the original gntI gene, N1 (5'-TAC-CGACAGTGGTCCCAAAG-3', SEQ ID NO 25) and N2 (5'-CCACCATGATATTCGGCAAG-3', SEQ ID NO 26) to detect the presence of the nptII cassette, GNT5F (5'-TGGGCTTTAACACAACTTTT-3', SEQ ID NO 27) and N3 (5'-TGTCGTGCTCCACCATGTT-3', SEQ ID NO 28) to control the integration of the transgene at the 5' end, and N4 (5'-GTTGAGCATATAAGAAAC-3', SEQ ID NO 29) and GNT10R (5'-CACATTGTTCAATTTGATAGAC-3', SEQ ID NO 30) to control the integration at the 3' end. Plants that gave the expected fragments in all four PCR reactions were considered as putative knockouts and selected for further analysis.

Finally 9 transgenic plants were chosen for further molecular and biochemical analysis.

1.4 Northern Analysis

Total RNA was isolated from moss tissue by RNeasy kit (Qiagen, Germany). For northern analysis, 5 microgram of total RNA were subjected to electrophoresis on formaldehyde-agarose gels, at 120V, transferred to Hybond-N nylon membranes (Amersham Biosciences), and hybridized with a $^{32}$P-labeled cDNA probe corresponding to 3' gntI cDNA including part of the homologous region used for the knock out and part of the cDNA not present on the knockout construct. The membranes were washed four times at different concentrations of SSC (the final washing step being 0.5×SSC, 0.1% SDS at 65° C.) and exposed to x-ray film (Kodak Bio-Max MS) at −80° C. for 2 to 3 days.

Northern analysis with the probe [obtained by PCR on the cDNA with primers: 3RACEG1 (5'-TTATCCGACCT-GAAGTTTGC-3', SEQ ID NO 13) and GNT15R (5'-AGTTTCTATGGTATCTAACTGC-3', SEQ ID NO 18)] detected the correct GNTI transcript solely in the wild type. The lack of the correct transcript in the knockout plants corroborates the disruption of the gntI gene in *P. patens*.

The expression of the control gene L21 was not affected in the transformants.

1.5. Southern Analysis of the Transgenic Plants

For Southern blot analysis 5 microgram of genomic DNA were used. For the detection of the number of integration sites for the nptII cassette the genomic DNA was digested with PvuII which cuts nptII cassette into two fragments and hybridized with the nptII cassette as a probe. This analysis showed that some plants have very high numbers of integrated selection cassettes whereas plant No. 6 has a single integration event. Plants No. 4 and 8 have also a low number of integrations: between 4-5 per plant.

In a second Southern analysis, genomic DNA was digested with EcoRI and hybridized with gntI probe located on the 3' end of the gene, out of the region which was used for creating the knockout construct. In this case it was expected that transgenic plants will have a band which is larger than WT for the size of the nptII cassette (1500 bp). WT have single signal at 4500 bp whereas transgenic plants have the bands of 6000 bp or other but do not contain the WT band, confirming disruption of the WT locus.

1.6 MALDI-TOF Mass Spectrometry

The N-glycans of *Physcomitrella patens* WT exhibit the typical structural features of plant N-glycans as described in e.g. Wilson et al. (2001) Glycobiology 11, 261-274). I.e. fucose in alpha 1,3-linkage to the Asn-bound GlcNAc, xylose in beta 1,2-linkage to the beta mannosyl residue, Lewis A epitopes (alpha 1,4-fucosyl and beta 1,3-galactosyl residues linked to GlcNAc) as non reducing terminal elements (tab. 1). Three GNTi knockout plants were analysed. The N-glycans of GNTI knockout plants exhibited the same structures compared to WT (tab. 1) confirming that the knockout was only successful on the molecular but not on the biochemical level. Therefore, it is assumed that another GNTI exists in *Physcomitrella patens*.

2. Cloning of the Alpha 1,3-fucosyltransferase from *P. patens* and Analysis of the Knockout Plants 2.1. Cloning of the cDNA and Genomic DNA for Alpha 1,3-fucosyltransferase (Alpha 1,3-FT)

Part of the cDNA for the alpha 1,3-FT was obtained by performing two rounds of PCR with degenerated primers on the cDNA from *P. patens* WT. These primers were created on the basis of a protein alignment of the known alpha 1,3-FTs from *Vigna radiata* and *Arabidopsis thaliana*. In the first round primers FD4F (5'-TGGGCNGARTAYGAYATGATG-3', SEQ ID NO 31) and FDR1 (5'-TGNGTNARNCCNAD-NGGRTADAT-3', SEQ ID NO 32) were used and then the product from this PCR was subjected to a subsequent PCR with the primers FD4F and FD5R (5'-TGNACNGCNGCC-ATRTC-3', SEQ ID NO 33). The second PCR resulting in a 510 bp product which was cloned into pCR 4 TOPO and sequenced from both ends.

To obtain the missing 5'-end of the cDNA, 5' RACE was performed with the primers: 5FT4 (5'-GTAACATTCGCAT-AATGG-3', SEQ ID NO 34), 5FT5 (5'-CGATCATTATGCG-CACCAC-3', SEQ ID NO 35), and 5FT6 (5'-GGAAATAAAAGCAGCTCC-3', SEQ ID NO 36) which gave an additional 200 bp of cDNA, however still without the initial Met. Therefore, on the base of the new sequence a second round of 5' RACE was performed with the primers: 5FT7 (5'-AGGGTGAATCTCCATAGCC-3', SEQ ID NO 37), 5FT8 (5'-CATCTGCCTGACCCTCACC-3', SEQ ID NO 38), and 5FT9 (5'-GCCTTGAACACGCATGGC-3', SEQ ID NO 39) which gave an additional 150 bp fragment but still without the initiation codon. Finally, a third round was performed with the primers: 5FT9, 5FT10 (5'-CGATA-CAACCAGCACAGG-3', SEQ ID NO 40), and 5FT11 (5'-CTTCTCTAGCCATTCTGCC-3', SEQ ID NO 41) which gave an additional 400 bp of sequence containing the initiation codon.

To obtain missing 3'-end of the cDNA 3' RACE was performed correspondingly with the primers: 3FT1 (5'-GCAGTGGAAGTTTAATGGTC-3', SEQ ID NO 42) and 3FT2 (5'-TCGTTTCTAGCTCTAGTAGAC-3', SEQ ID NO 43) which resulted in a fragment of about 550 bp with the stop codon and finally the complete 1711bp of the cDNA for the alpha 1,3-FT (GenBank: partial cDNA: AJ429145).

The corresponding 3083 bp of the genomic sequence was obtained by cloning the alpha 1,3-FT gene in three pieces by PCR from WT *P. patens* genomic DNA with the specific primers: FTA9F (5'-ATGCTCCCAGCCCAAGAC-3', SEQ ID NO 44) and FTA10R (5'-TGTCTACTAGAGCTA-GAAACG-3', SEQ ID NO 45), FT18F (5'-TAGGGAG-TAAATATGAAGGG-3', SEQ ID NO 46) and 5FT5 (5'-CGATCATTATGCGCACCAC-3', SEQ ID NO 35), 3FT1 (5'-GCAGTGGAAGTTTAATGGTC-3', SEQ ID NO 42) and FTA12R (5'-TACTTCCAATTGAAGACAAGG-3', SEQ ID NO 47) which were sequenced by primer walking.

2.2. Creating the Knockout Construct for Alpha 1,3-FT

To create the knockout construct, PCR on the genomic DNA was performed with the primers: FT15F (5'-AATGT-TCTGTGCCATGCG-3', SEQ ID NO 48) and FT16R (5'-TGCTTCAAATGGGCTAGGG-3', SEQ ID NO 49). The thus obtained 2156 bp fragment was cloned into the pCR4 TOPO (Invitrogen, USA) vector. The NptII cassette was synthesized by PCR with a proof reading polymerase on the pRT101neo plasmid (Girke et al. 1998) with the primers: nptII/NdeI-F (5'-ATGCCATATGGCATGCCTGCAGGT-CAAC-3', SEQ ID NO 50) to generate a NdeI restriction site and nptII/BstZ17I-R (5'-GCATGTATACGCATGCCTG-CAGGTCACTG-3', SEQ ID NO 51) to generate a BstZ17I site. The PCR product was also cloned into pCR4 TOPO (Invitrogen, USA). Both plasmids were digested with NdeI and BstZ17I restriction enzymes. By this restriction a 195 bp, fragment containing a part of the fourth intron and a part of the fifth exon was cut out from the alpha 1,3-FT genomic fragment and replaced by the nptII cassette.

For the transformation of *P. patens* resulting the knockout construct was digested with NotI and MssI restriction enzymes and 25 microgram were used for transformation.

2.3. Pre-Screening of the Transgenic Plants

For the pre-screening of the resistant plants, small pieces of gametophores (1-5 mg) were treated for 30 min at 45° C. in 75 mM Tris-HCl, pH 8 containing 20 mM $(NH_4)_2SO_4$, and 0.1% Tween 20, and 3 microliter of this extract was used for PCR with the following four pairs of primers: FT14F (5'-ACAAAGTTACATACTCGCG-3', SEQ ID NO 52) and FTA12R (5'-TACTTCCAATTGAAGACAAGG-3', SEQ ID NO 47) to detect a disruption of the original ft gene, N1 (5'-TACCGACAGTGGTCCCAAAG-3', SEQ ID NO 25) and N2 (5'-CCACCATGATATTCGGCAAG-3', SEQ ID NO 26) to detect the presence of the nptII cassette, FT14F (5'-ACAAAGTTACATACTCGCG-3', SEQ ID NO 52) and N3 (5'-TGTCGTGCTCCACCATGTT-3', SEQ ID NO 28) to control the integration of the transgene at the 5' end, FTA12R (5'-TACTTCCAATTGAAGACAAGG-3', SEQ ID NO 47) and N4 (5'-GTTGAGCATATAAGAAAC-3', SEQ ID NO 29) to control the integration at the 3' end. Plants that gave the expected fragments by all four PCR reactions were considered as putative knockouts and selected for further analysis.

Finally 9 plants were chosen for further molecular and biochemical analysis.

2.4. RT-PCR

Total RNA was isolated from moss tissue by RNeasy kit (Qiagen, Germany). Reverse transcription PCR was performed according to standard protocol. For the RT-PCR primers FTA9F (5'-ATGCTCCCAGCCCAAGAC-3', SEQ ID NO 44) and FTA10R (5'-TGTCTACTAGAGCTAGAAACG-3', SEQ ID NO 45) located in the central region of the cDNA for alpha 1,3-FT were used. Using these primers a 475 bp transcript was detected only in the WT whereas all transgenic plants did not give any PCR products. The absence of the detectable transcript with the primers located on both sides of integrated nptII cassette confirms that all plants analysed are knockouts.

As a control RT-PCR was performed with primers for APS reductase (Koprivova et al. (2002) J. Biol. Chem. 277, 32195-32201): R10 (5'-TCTTTCACTATTCGGTGACG-3', SEQ ID NO 53) and R11 (5'-CGACCACAACATTAGATCC-3', SEQ ID NO 54), which amplified a 900 bp fragment from all plants.

2.5 MALDI-TOF Mass Spectrometry

The N-glycans of *Physcomitrella patens* WT exhibit the typical structural features of plant N-glycans as described in e.g. Wilson et al. (2001), supra. I.E. fucose in alpha 1,3-linkage to the Asn-bound GlcNAc, xylose in beta 1,2-linkage to the beta mannosyl residue, Lewis A epitopes (alpha 1,4-fucosyl and beta 1,3-galactosyl residues linked to GlcNAc) as non reducing terminal elements (tab. 1). Three alpha 1,3 FT knockout plants were analysed. No alpha 1,3 fucose residues linked to the Asn-bound GlcNAc could be detected on the N-glycans of alpha 1,3 FT knockout plants (tab. 1) confirming that the knockout of alpha 1,3 fucosyltransferase in *Physcomitrella patens* was completely successful.

2A. Cloning of the Alpha 1,3-fucosyltransferase Flanking Regions from *P. patens* and Construction of the Knockout Constructs 2A.1. Cloning of Flanking DNA Corresponding to the Alpha 1,3-fucosyltransferase (Alpha 1,3-FT) Gene The 3'-flanking DNA corresponding to the alpha 1,3-fucosyltransferase gene of *Physcomitrella patens* was amplified by PCR from genomic DNA using primer MoB558 (5'-GTTCCGCGGTGATCCCGTTTTCATATCAGTGTATT-3', SEQ ID NO 84) containing a SacII restriction site and primer MoB557 (5'-TTTGAGCTCTACGTAACAATAACATAAAATATCACA-3', SEQ ID NO 85), containing a SnaBI and a SacI site. The PCR product (5'-GTTCCGCGGTGATCCCGTTTTCATATCAGTGTATTATCATCAGTGACTGCATATTGACACCCAATTCTGATGATTTTTATTTTTTATTTTTTATTTTTTTGGTATGGTTACA TGCTTTTCAGAGGTTTCTATGCCGCTGAGTATTTTCCTGAATCGCGAGGTGTGACAGGTTATCT GCGCCGTCCACdCAATATTTTATGATGAGTCGATGATTCGTGAGACTAATCTAGCTTAACCTTT TTCTTACTGGCAAGTCAAAATTGAGTTTAAAATATTTCAGTATCCTGTTAGTAATTTCAGACACATGTATTCTATGTCTCATACTCTTTACGTGAAAGTTCAACTGACTTATATTTTGTCGTTTTCT GTAGATCACTGTTTAGCGCATACAAAGACAATTGTCTAAATATTTTAAAGAAGGTGATATTT TATTATAAGATAGAAGTCAATATGTTTTTTTGTTATGCACATGACTTGAATAAAATAAATTTTT TTGTTAGATTTAAATACTTTTTGAATTATAGCTTTGTTGAAATTAAGGAATTTATATTCATAAG AAGCTACTCGAACAAATTTACAAAGAGAACATTTGATAAGTAAAAGTAATTAAAAGTTTTTTTT AATTTAAAAAGATTAATTTTTATTAATAAGAAGAACTTGGAAAGTTAGAAAAATATTTAACTTT AAAAATTAAGAAAACAAGGCAAAACTTTAATTTACAAATACTTAATGTAGATTAATTTTCTTAT TATATATTAGCACAAATTATCATTATGTGATATTTTATGTTATTGTTACGTAGAGCTCAAA-3', SEQ ID NO 86) was digested with SacI and SacII and cloned into the plasmid pBS (SacI/SacII digested).

The 5'-flanking DNA corresponding to the alpha 1,3-fucosyltransferase gene of *Physcomitrella patens* was amplified by PCR from genomic DNA using primer MoB555 (5'-CGCGTTAACTCTCTCTATCTCTCTCTGTGTTGCG-3', SEQ ID NO 87) containing a HincII restriction site and primer MoB556 (5'-CGAGAATTCTCACTTAGAAGAAGCCCAATCCT-3', SEQ ID NO 88) containing an EcoRI site. The PCR product (5'-CGCGTTAACTCTCTCTATCTCTCTCTGTGTTGCGTTTGATCAGGGGTTTTAGGGTTTGGGTCCA GGGTTCCGAGGAGTATCGTCACGTGTATTGCGGTCTTGTTGGAGATTCCTCAGTTGTGCATGTA GATATAAACTTAGTTTAGTCCACGATCGGTTTCTAATCGTGGATTTTTGTGGGTTTCGGTCGTT GAGCAAGAATTTTGTGAATTTTTTGTATTGGGGGAAGGAAATGGGGTTATGGCGATATCGTTTT CGTTGGGTTCAACGTGATCGGTGAGCTCCAGGAAGGGCTGGTCACTCACAATCCGGTATTCGTCTCATCGAGACGCATTTATCGGTTCATTATATGTATATATATATATATATATATATGCAGAGTCGATTGTTGTTGCAATTTCTGAACTAGGTACTGTTGAATTGTAGATTGCCTTCAAGTAGCTCTCGAT GTTGGAATGACGSACACAAATTCTGCTACTGAATGAGACCATATTCTGCACCGTTAATTGGTTT TATGAATATATGGTGTCGAATTACATTCTGTCTCGAATCCATGCGCCCTTTCTGCACGAACGTT GGTTTGTAGTTGTAGTGCAGCCAGTGTGTTTGGTTTAGGATTATGCTTTGACGATCGATGAGTC CGTTTCATGGTTTTATACTTGTCATTTATCTTCTTGTGATTTTTTGTTTACAAATGTTCCCCCA ATTGTAACGTGGGACTTTCGTGTGTGGTGGTTGCTCAAATTGATAGTTTTGGTCATTTGATTTG CGGAGAGCAATCGGTGTCATGGAAAATCCCTTCGACTGCTTTGATCCAATCAAAGTTCTGCTTG AGCCAATGTGAGAGGTGGAGGATTGGGCTTCTTCTAAGTGAGAATTCTCG-3', SEQ ID NO 89) was digested with HincII and EcoRI and cloned into the plasmid pBS containing the 3'-flanking DNA corresponding to the alpha 1,3-fucosyltransferase gene of *Physcomitrella patens* (HincII/EcoRI digested).

2A.2. Creating the Knockout Construct for the Replacement of the Alpha 1,3-FT Gene To create the knockout construct a expression cassette containing the 35 S promoter, the 297 bp ftsz1 cDNA fragment coding for the FtsZ1 chloroplast transit peptide of *Physcomitrella patens*, the coding sequence for GFP and the nos terminator (Kiessling et al. (2000) J. Cell Biol. 151, 945-950) was used. The expression cassette was subcloned into pZERO by digestion of pFtsZ1(1-93)-GFP with HindIII and EcoRI and cloning into HindIII/EcoRI digested pZERO, resulting in the plasmid pZEROftszGFP. The expression cassette was cut out from pZEROftszGFP by digestion with HindIII, blunting by incubation with Klenow fragment and subsequently digestion with EcoRI. To create the knockout construct, the digested expression cassette was cloned into the vector described in 2A.1 which was digested with SmaI and EcoRI.

The final plasmid was digested with Kpn I/Sna BI resulting in the linearised DNA containing the 3'-flanking DNA corresponding to the alpha 1,3-fucosyltransferase gene of *Physcomitrella patens*, TPftsZGFP fusion gene under the control of the 35S promoter and the nos terminator and the 5'-flanking DNA corresponding to the alpha 1,3-fucosyltransferase gene of *Physcomitrella patens*. This linearised plasmid was used for the knockout of the alpha 1,3-fucosyltransferase gene of *Physcomitrella patens*.

2A.3. Generating Plants with Alpha 1,3 fucosyltransferase and Beta 1,2 xylosyltransferase Knockouts For generating plants without alpha 1,3-fucosyl and beta 1,2-xylosyl residues protoplasts derived of *Physcomitrella patens* protonema were transformed with the constructs described in chapters 2A and 3. Transformation could be performed subsequently as well as co-transformation with both constructs. In this case the knockout of the alpha 1,3-fucosyltransferase gene was performed not only by a gene disruption but by a gene replacement. As an additional selection marker in the subsequent transformation procedure a plasmid containing the gene responsible for hygromycin resistance (pCambia1305) was used for cotransformation.

2A.4 MALDI-TOF Mass Spectrometry

The N-glycans of *Physcomitrella patens* WT exhibit the typical structural features of plant N-glycans as described in e.g. Wilson et al. (2001), supra. I.e. fucose in alpha 1,3-linkage to the Asn-bound GlcNAc, xylose in beta 1,2-linkage to the beta mannosyl residue, Lewis A epitopes (alpha 1,4-fucosyl and beta 1,3-galactosyl residues linked to GlcNAc) as non reducing terminal elements (Tab. 1). One transgenic plant was analysed. No alpha 1,3 fucosyl residues linked to the Asn-bound GlcNAc nor beta 1,2-xylosyl residues could be detected on the N-glycans of these plants.

3. Cloning of the Beta 1,2-xylosyltransferase from *P. patens* and Analysis of the Knockout Plants

3.1. Cloning of the cDNA and Genomic DNA for Beta 1,2-xylosyltransferase (Beta 1,2 XT)

Part of the cDNA for the beta 1,2-XT was obtained by performing two rounds of PCR with degenerated primers on the cDNA from *P. patens* WT. These primers were created on the basis of a protein alignment of the known beta-1,2-XTs from plants. In the first round primers XDF1 (5'-TGYGARG-SNTAYTTYGGNAAYGG-3', SEQ ID NO 55) and XDR1 (5'-GCNCKNAYCATYTCNCCRAAYTC-3', SEQ ID NO 56) were used and then the product from this PCR was subjected to a subsequent PCR with the primers XDF2 (5'-GGNGGNGARAARYTNGARRANGT-3', SEQ ID NO 57) and XDR1. The second PCR gave a 610 bp product which was cloned into pCR 4 TOPO (Invitrogen, USA) and sequenced from both ends.

To obtain the missing 5'-end of the cDNA, 5' RACE was performed with the primers: 5XT1 (5'-TCCTCCT-TCTCTGGGACC-3', SEQ ID NO 58), 5XT2 (5'-AGCTC-CAGTTGTGAAATATGG-3', SEQ ID NO 59) and 5XT3 (5'-TTCTTCCTCATTTCGTCCC-3', SEQ ID NO 83) which gave an additional 360 bp of cDNA, however still without the initial Met. Therefore, on the basis of the new sequence a second round of 5' RACE was performed with the primers: 5XT4 (5'-CTTCCTTCACCACACTAC-3', SEQ ID NO 60), 5XT5 (5'-TAGCATGACTGTGTGGCC-3', SEQ ID NO 61) and 5XT6 (5'-AAAGGCTTGAGTGTAGCC-3', SEQ ID NO 62) which gave an additional 390 bp fragment containing the initiation codon.

To obtain missing 3'-end of the cDNA 3' RACE was performed correspondingly with the primers: 3XT1 (5'-GC-CTTTCTTGCACGGGTTG-3', SEQ ID NO 63) and 3XT2 (5'-GGACATTCCAAATAATCCC-3', SEQ ID NO 64) which resulted in a fragment of about 940 bp with the stop codon and finally the complete 2300 bp of the cDNA for beta 1,2-XT (GenBank: 1788 bp corresponding to the coding region: AJ 429144). The 2388 bp of the genomic sequence was obtained by cloning the beta 1,2-XT gene in three pieces by PCR on WT *P. patens* genomic DNA with the specific primers: XT14F (5'-TTACGAAGCACACCATGC-3', SEQ ID NO 82) and XT15R (5'-GTCCTGTTAAATGCCTTGC-3', SEQ ID, NO 65), XT-M1F (5'-AGGTTGAGCAATCATATGGC-3', SEQ ID NO 66) and 5XT2, 3XT1 and XT11R (5'-ATCCCA-GAAATATCTGATCC-3', SEQ ID NO 67) which were sequenced by primer walking.

3.2. Creating the Knockout Construct for Beta 1,2-XT

To create the knockout construct PCR on the genomic DNA was performed with the primers: XT12F (5'-TGTGAG-GCGTTCTTTGGC-3', SEQ ID NO 68) and XT11R (5'-ATC-CCAGAAATATCTGATCC-3', SEQ ID NO 67). The thus obtained fragment of 20.66 bp fragment was cloned into pCR4TOPO vector (Invitrogen, USA). The nptII cassette was synthesized by PCR on the pRT101neo plasmid (Girke et al. 1998) by proof reading polymerase with the primers: nptII/SalI-F (5'-ATGCGTCGACGTCAACATGGTGGAGCACG-3'. SEQ ID NO 69) for creating SalI restriction site and nptII/NdeI-R (5'-GCATCATATGTCACTGGATTTTG-GTTTTAGG-3', SEQ ID NO 70) for creating NdeI site. The PCR product was also cloned into pCR4TOPO (Invitrogen, USA). Both plasmids were digested with NdeI and SalI restriction enzymes. From the plasmid with genomic DNA a 380 bp fragment containing part of the second exon and part of the second intron was cut out and replaced by the nptII cassette was introduced.

For the transformation of *P. patens* the resulting knockout construct was digested with NotI and SpeI restriction enzymes and 25 microgram were used for transformation.

3.3. Pre-Screening of the Transgenic Plants

For the pre-screening of the resistant plants, small pieces of gametophores (1-5 mg) were treated for 30 min at 45° C. in 75 mM Tris-HCl, pH 8 containing 20 mM $(NH_4)_2SO_4$ and 0.1% Tween 20, and 3 microliter of this extract was used for PCR with the following four pairs of primers: XT-M1F (5'-AGGT-TGAGCAATCATATGGC-3', SEQ ID NO 66) and XT13R (5'-ACGATCCAAAATCTGGACGC-3', SEQ ID NO 71) to detect a disruption of the original xt gene, N1 (5'-TACCGA-CAGTGGTCCCAAAG-3a, SEQ ID NO 25) and N2 (5'-CCACCATGATATTCGGCAAG-3', SEQ ID NO 26) to detect the presence of the nptII cassette, XT-MLF (5'-AGGT-TGAGCAATCATATGGC-3', SEQ ID NO 66) and N3 (5'-TGTCGTGCTCCACCATGTT-3', SEQ ID NO 28) to control the integration of the transgene at the 5' end, XT13R (5'-ACGATCCAAAATCTGGACGC-3', SEQ ID NO 71) and N4 (5'-GTTGAGCATATAAGAAAC-3', SEQ ID NO 29) and to control the integration at the 3' end. Plants that gave the expected fragments in all four PCR reactions were considered as putative knockouts and selected for further analysis.

Finally 9 plants were chosen for further molecular and biochemical analysis.

3.4. RT-PCR

Total RNA was isolated from moss tissue by RNeasy kit (Qiagen, Germany). Reverse transcription PCR was performed according to standard protocol. For the RT-PCR primers XT14F (5'-TTACGAAGCACACCATGC-3', SEQ ID NO 82) and XT15R (5'-GTCCTGTTAAATGCCTGC-3', SEQ ID NO 65) located in the central region of cDNA for beta 1,2-XT and on both sides of npt II cassette were used. Using these primers a 290 bp transcript was detected only in the WT whereas all transgenic plants did not give any PCR products. The absence of the transcript with the primers located on both sides of the integrated nptII cassette confirms that all plants analysed are knockouts.

As a control RT-PCR was performed with primers for APS reductase (Koprivova et al. 2002), supra): R10 (5'-TCTTTCACTATTCGGTGACG-3', SEQ ID NO 53) and R11 (5'-CGACCACAACATTAGATCC-3', SEQ ID NO 54), which amplified a 900 bp fragment from all plants.

3.5 MALDI-TOF Mass Spectrometry

The N-glycans of *Physcomitrella patens* WT exhibit the typical structural features of plant N-glycans as described in e.g. Wilson et al. (2001), supra). I.e. fucose in alpha 1,3-linkage to the Asn-bound GlcNAc, xylose in beta 1,2-linkage to the beta mannosyl residue, Lewis A epitopes (alpha 1,4-fucosyl and beta 1,3-galactosyl residues linked to GlcNAc) as non reducing terminal elements (tab. 1). Three beta 1, 2XT knockout plants were analysed. No beta 1,2 xylosyl residues linked to the beta-mannosyl residue could be detected on the N-glycans of beta 1,2 XT knockout plants (tab. 1) confirming that the knockout of beta 1,2 xylosyltransferase in *Physcomitrella patens* was completely successful.

4. Cloning of the cDNA for Human Beta-1,4-galactosyltransferase cDNA from human liver (Invitrogen, USA) was used for isolation of beta 1,4-galactosyltransferase (GalT, GenBank: X55415) cDNA. By using 5' primer GalTXh-F (5'-TTCTC-GAGACAATGAGGCTTCGGGAGCCGCTC-3', SEQ ID NO 72) containing a Xho I restriction site and 3' primer GalTXb-R (5'-GGTCTAGACTAGCTCGGTGTCCCGAT-GTCC-3', SEQ ID NO 73) containing a Xba I restriction site for PCR with Elongase enzyme mix (Invitrogen, USA) a 1.2 kb DNA fragment was amplified. The 1.2 kb fragment was cloned into pCR4-TOPO (Invitrogen, USA). The fragment was cut out from this vector with Xho I and Xba I and cloned into pRT101 (Topfer et al. (1987) NAR 15, 5890) digested with Xho I and Xba I. The resulting plasmid pRT101-GalT contained the cDNA of human beta 1,4-galactosyltransferase under the control of CaMV 35S promoter and CaMV terminator.

5. Creating the Knockout Construct for Beta 1,2-xylosyltransferase and Integration of Human Beta 1,4-galactosyltransferase From genomic DNA of *Physcomitrella patens* a 1.56 kb fragment of the beta 1,2-xylosyltransferase gene was amplified by using primer XTB-F (5'-TTGGATCCTCAATTAC-GAAGCACACCATGC-3', SEQ ID NO 74) and primer XTB-R (5'-TTGGATCCTCCTCCCAGAAACATCT-GATCCAG-3', SEQ ID NO 75), both primers introduced Bam HI restriction sites. The amplification product was cloned into pCR4-TOPO (Invitrogen, USA). The cloned beta-1,2-xylosyltransferase gene fragment contained a single Hind III restriction site. In this Hind III restriction site the cDNA of beta 1,4-galactosyltransferase under the control of CaMV 35S promoter and CaMV terminator was introduced by ligation, resulting in the plasmid pCR4-XTko-GalTki. Digestion of pCR4-XTko-GalTki with Bam HI resulted in a fragment which contained the cDNA of beta 1,4-galactosyltransferase under the control of CaMV 35S promoter and CaMV terminator flanked 5' and 3' by sequences homolog to the beta 1,2-xylosyltransferase gene of *Physcomitrella patens*. This fragment was used for knock out experiments.

5.1 PCR

For PCR analyses genomic DNA isolated from the putative knockout plants was used. The primers MoB 521 (5'-TTGC-CGCTATCTACTTGTATGCTAACGT-3', SEQ ID NO 76) and MoB 575 (5'-TGCCGTGGATGTGCTAGATAATCTT-3', SEQ ID NO 77) were located on the sequences homologous to the beta 1,2-xylosyltransferase on both sides of the beta 1,4-galactosyltransferase cassette. A fragment of 339 bp corresponding to the expected beta 1,2-xylosyltransferase sequence was amplified from WT. From knockout plants a 2.1 kbp fragment corresponding to the introduced beta 1,4-galactosyltransferase cassette was amplified and no 339 bp fragment could be detected, confirming the knockout of beta 1,2-xylosyltransferase as well as the integration of the beta 1,4-galactosyltransferase cassette.

5.2 MALDI-TOF Mass Spectrometry

The N-glycans of *Physcomitrella patens* WT exhibit the typical structural features of plant N-glycans as described in e.g. Wilson et al. (2001), supra. I.e. fucose in alpha 1,3-linkage to the Asn-bound GlcNAc, xylose in beta 1,2-linkage to the beta mannosyl residue, Lewis A epitopes (alpha 1,4-fucosyl and beta 1,3-galactosyl residues linked to GlcNAc) as non reducing terminal elements (tab. 1). Three beta 1,2XT knockout, beta 1,4 GT integration plants were analysed. No beta 1,2 xylosyl residues linked to the beta-mannosyl residue could be detected on the N-glycans of these plants. The peak at 2235 found in WT describing the (GF) (GF)XF structure was shifted in the N-glycan pattern of the transgenic plants confirming the activity of the human beta 1,4 galactosyltransferase in *Physcomitrella patens*.

6. Creating the Knockout Construct for Alpha 1,3-fucosyltransferase and Integration of Human Beta 1,4-galactosyltransferase From genomic DNA of *Physcomitrella patens* a 2.66 kb fragment of the alpha 1,3-fucosyltransferase gene was amplified by using primer FTB-F (5'-TAGGATCCAGATGAT-GTCTGCTCGGCAGAATGG-3', SEQ ID NO 78) and primer FTB-R (5'-CTGGATCCTTGTAGATCCGAAG-GTCTGAGTTCC-3', SEQ ID NO 79), both primers introduced Bam HI restriction sites. The amplification product was cloned into pCR4-TOPO (Invitrogen, USA). The cloned alpha 1,3-fucosyltransferase gene fragment contained two Hind III restriction sites. In these Hind III restriction sites the cDNA of beta 1,4-galactosyltransferase under the control of CaMV 35S promoter and CaMV terminator was introduced by ligation, resulting in the plasmid pCR4-FTko-GalTki. Digestion of pCR4-FTko-GalTki with Bam HI resulted in a fragment which contained the cDNA of beta 1,4-galactosyltransferase under the control of CaMV 35S promoter and CaMV terminator flanked 5' and 3' by sequences homolog to the beta 1,3-fucosyltransferase gene of *Physcomitrella patens*. This fragment was used for knock out experiments.

6.1 PCR

For PCR analyses genomic DNA isolated from the putative knockout plants was used. The primers MoB 435 (5'-TC-CTACCTGCGGAGCAACAGATATTG-3', SEQ ID NO 80) and MoB 495 (5'-GTGGACCCAGATTTGCTGGTG-CACTTG-3', SEQ ID NO 81) were located on the sequences homologous to the alpha 1,3-fucosyltransferase on both sides of the beta 1,4-galactosyltransferase cassette. A fragment of 2 kbp corresponding to the expected alpha 1,3-fucosyltransferase sequence was amplified from WT. From knockout plants a 2.8 kbp fragment corresponding to the introduced beta 1,4-galactosyltransferase cassette was amplified and no 2 kbp fragment could be detected, confirming the knockout of alpha 1,3-fucosyltransferase as well as the integration of the beta 1,4-galactosyltransferase cassette.

6.2 MALDI-TOF Mass Spectrometry

The N-glycans of *Physcomitrella patens* WT exhibit the typical structural features of plant N-glycans as described in e.g. Wilson et al. (2001), supra. I.e. fucose in alpha 1,3-linkage to the Asn-bound GlcNAc, xylose in beta 1,2-linkage to the beta mannosyl residue, Lewis A epitopes (alpha 1,4-fucosyl and beta 1,3-galactosyl residues linked to GlcNAc) as non reducing terminal elements (tab. 1). Three alpha 1,3 FT knockout, beta 1,4 GT integration plants were analysed. No alpha 1,3 fucosyl residues linked to the Asn-bound GlcNAc could be detected on the N-glycans of these plants. The peak at 2235 found in WT describing the (GF) (GF)XF structure was shifted in the N-glycan pattern of the transgenic plants confirming the activity of the human beta 1,4 galactosyltransferase in *Physcomitrella patens*.

7. Generating Plants with Alpha 1,3 fucosyltransferase and Beta 1,2 xylosyltransferase Knockouts and Beta 1,4-galactosyltransferase Integration For generating plants without alpha 1,3-fucosyl and beta 1,2-xylosyl residues and with beta 1,4 linked galactosyl residues protoplasts derived of *Physcomitrella patens* protonema were transformed with the constructs described in chapter 5 and 6. Transformation could be performed subsequently as well as co-transformation with both constructs.

7.1 PCR

For PCR analyses same procedures as described in 5.1 and 6.1 were performed.

7.2 MALDI-TOF Mass Spectrometry

The N-glycans of *Physcomitrella patens* WT exhibit the typical structural features of plant N-glycans as described in e.g. Wilson et al. (2001), supra. I.e. fucose in alpha 1,3-linkage to the Asn-bound GlcNAc, xylose in beta 1,2-linkage to the beta mannosyl residue, Lewis A epitopes (alpha 1,4-fucosyl and beta 1,3-galactosyl residues linked to GlcNAc) as non reducing terminal elements (tab. 1). Three transgenic plants were analysed. No alpha 1,3 fucosyl residues linked to the Asn-bound GlcNAc nor beta 1,2-xylosyl residues could be detected on the N-glycans of these plants. The peak at 2235 found in WT describing the (GF) (GF)XF structure was shifted to mass peak of 1665 in the N-glycan pattern of the transgenic plants confirming the activity of the human beta 1,4 galactosyltransferase in *Physcomitrella patens* as well as the loss of 1,3 linked fucosyl and 1,2 linked xylosyl residues.

8.1 Purification and Analysis of Recombinant Human VEGF$_{121}$ Expressed in Transiently Transformed *Physcomitrella* Protoplasts Protoplasts derived from protonema of transgenic *Physcomitrella* plants containing human beta 1,4 galactosyltransferase and no alpha 1,3 fucosyltransferase nor beta 1,2 xylosyltransferase (7.2) were transformed with pRT101TPVEGF C3. Expressed VEGF$_{121}$ was secreted into the medium. After two, three and four days the culture medium was collected and replaced by fresh medium. Samples were filtered through a 0.22 microm Millex GP filter unit (Millipore). Recombinant VEGF$_{121}$ was purified by FPLC (Äktaexplorer 100, Amersham Biosciences, Germany) using a SP-Sepharose column (Amersham Biosciences, Germany). Elution was performed with sodium chloride in 25 mM Na-acetate, pH 5.0. Eluted fractions were concentrated by centrifugation using Amicon Ultra filter devices, cut off 10.000 (Millipore).

SDS/PAGE loading buffer was added to the samples, proteins were fractionated on SDS/PAGE containing 15% acrylamide and 0.4% bisacrylamide. Gels were stained with Coomassie Brilliant Blue R-250. VEGF121 band was excised from Coomassie stained SDS/PAGE and digested with sequencing grade trypsin. The glycans were released by treatment with peptide:N-glycosidase A and analysed by MALDI-TOF mass spectrometry on a DYNAMO (Thermo BioAnalysis, Santa Fe, N. Mex.).

Detected N-glycan pattern of secreted recombinant VEGF$_{121}$ was similar to that observed in transgenic GalT (with knockouts of FucT and XylT, see 7.2) plants confirming the activity of the human beta 1,4 galactosyltransferase in *Physcomitrella patens* as well as the loss of 1,3 linked fucosyl and 1,2 linked xylosyl residues.

The following Tab. 1 shows the N-glycan structures of *Physcomitrella patens* wildtype (wt) and knock out plants. N-glycans were isolated from plant material grown under same conditions (500 ml flasks, modified Knop medium). F=fucosyl residue, G=galactosyl residue, Gn=N-acetylglucosaminyl residue, M/Man=mannosyl residue, X=xylosyl residue. (GF) (GF)XF depicts the most complex type N-glycan, the so called Lewis a formation.

| M + Na | WT Structures normal | GNT1 Ko Structures normal | FucT Ko Structures without α-1,3-fucosyl residues | XylT Ko Structures without β-1,2-xylosyl residues | XylT Ko + FucT Ko Structures without α-1,3-fucosyl res. and β-1,2-xylosyl residues |
|---|---|---|---|---|---|
| 933.8 | Man3 (MM) | Man3 (MM) | Man3 (MM) | Man3 (MM) | Man3 (MM) |
| 1065.7 | MMX | MMX | MMX | | |
| 1080.0 | MMF | MMF | | MMF | |
| 1096.0 | Man4 | Man4 | Man4 | Man4 | Man4 |
| 1137.0 | MGn/GnM | MGn/GnM | MGn/GnM | MGn/GnM | MGn/GnM |
| 1212.1 | MMXF | MMXF | | | |
| 1227.8 | Man4X | Man4X | | | |
| 1258.4 | Man5 | Man5 | Man5 | Man5 | Man5 |
| 1269.1 | GnMX/MGnX | GnMX/MGnX | GnMX/MGnX | | |
| 1283.4 | | | | GnMF/MGnF | |
| 1299.2 | Man4Gn | Man4Gn | Man4Gn | Man4Gn | Man4Gn |
| 1340.2 | GnGn | GnGn | GnGn | GnGn | GnGn |
| 1415.5 | GnMXF/MGnXF | GnMXF/MGnXF | | | |
| 1420.2 | Man6 | Man6 | Man6 | Man6 | Man6 |
| 1431.4 | Man4GnX | Man4GnX | Man4GnX | | |
| 1445.3 | Man4GnF | Man4GnF | | Man4GnF | |
| 1460.3 | | | | | Man5Gn |
| 1472.1 | GnGnX | GnGnX | GnGnX | | |
| 1486.4 | GnGnF | GnGnF | | GnGnF | |
| 1577.4 | GMXF/MGXF/ Man4GnXF | GMXF/MGXF/ Man4GnXF | | | |
| 1582.4 | Man7 | Man7 | Man7 | Man7 | Man7 |
| 1618.5 | GnGnXF | GnGnXF | | | |
| 1648.6 | | | | | (GF)Gn/Gn(GF) |
| 1739.5 | Man5GnXF | Man5GnXF | | | |
| 1744.5 | Man8 | Man8 | Man8 | Man8 | Man8 |
| 1780.4 | | | (GF)GnX/ Gn(GF)X | | |
| 1794.9 | | | | (GF)GnF/ Gn(GF)F | |
| 1907.1 | Man9 | Man9 | Man9 | Man9 | Man9 |
| 1926.7 | (GF)GnXF/ Gn(GF)XF | (GF)GnXF/ Gn(GF)XF | | | |
| 1956.6 | | | | | (GF) (GF) |
| 2068.8 | Man9Glc1 | Man9Glc1 | | | |
| 2088.9 | | | (GF) (GF)X | | |
| 2102.8 | | | | (GF) (GF)F | |
| 2235.0 | (GF) (GF)XF | (GF) (GF)XF | | | |

The invention claimed is:

1. A transformed bryophyte cell from *Physcomitrella patens* that comprises i) a disrupted endogenous alpha 1,3-fucosyl transferase encoding nucleotide sequence and ii) a disrupted endogenous beta 1,2-xylosyl transferase encoding nucleotide sequence, whereby the bryophyte cell is incapable of forming N-linked glycans with 1,3-linked fucosyl and 1,2-linked xylosyl residues.

2. A transformed bryophyte cell according to claim 1, wherein the cell further comprises a nucleotide sequence operably linked to an exogenous promoter that drives expression in the bryophyte cell, wherein said nucleotide sequence encodes a glycosylated polypeptide that is expressed in the bryophyte cell.

3. A transformed bryophyte cell according to claim 1, further comprising a nucleotide sequence operably linked to an exogenous promoter that drives expression in the bryophyte cell, wherein said nucleotide sequence encodes a functional human beta 1, 4 galactosyltransferase that is expressed in the bryophyte cell, whereby the bryophyte cell is capable of forming N-linked glycans with terminal 1,4-linked galactosyl residues.

4. A transformed bryophyte cell according to claim 2, wherein said glycosylated polypeptide is a polypeptide having a primary amino acid sequence of a human glycosylated polypeptide or a primary amino acid sequence of an antibody or an active fragment thereof.

5. A transformed bryophyte cell according to claim 4, wherein said glycosylated polypeptide is selected from the group consisting of human insulin, preproinsulin, vascular endothelial growth factor (VEGF), proinsulin, glucagon, alpha-interferon, beta-interferon, gamma-interferon, blood-clotting factors VII, VIII, IX, X, XI, and XII, luteinising hormone, follicle stimulating hormone, epidermal growth factor, platelet-derived growth factor, granulocyte colony stimulating factor, prolactin, oxytocin, thyroid stimulating hormone, adrenocorticotropic hormone, calcitonin, parathyroid hormone, somatostatin, erythropoietin (EPO), beta-glucocerebrosidase, haemoglobin, serum albumin, and collagen.

6. A bryophyte plant or bryophyte tissue from *Physcomitrella patens* comprising a transformed bryophyte cell according to claim 1.

7. A transformed bryophyte cell according to claim 1, wherein said disrupted alpha 1,3-fucosyl transferase encoding nucleotide sequence and said disrupted beta 1,2-xylosyl transferase encoding nucleotide sequence are each independently disrupted by insertion of exogenous nucleic acids or by at least partial deletion of endogenous nucleic acids.

8. A transformed bryophyte cell according to claim 4, wherein said glycosylated polypeptide is selected from the group consisting of an interferon, a fertility hormone, a growth factor and an enzyme.

9. A transformed bryophyte cell according to claim 2, further comprising a nucleotide sequence operably linked to an exogenous promoter that drives expression in the bryophyte cell, wherein said nucleotide sequence encodes a functional human beta 1, 4 galactosyltransferase that is expressed in the bryophyte cell, whereby the bryophyte cell is capable of forming N-linked glycans with terminal 1,4-linked galactosyl residues.

10. A transformed bryophyte cell according to claim 9, wherein said glycosylated polypeptide is a polypeptide having a primary amino acid sequence of a human glycosylated polypeptide or a primary amino acid sequence of an antibody or an active fragment thereof.

11. A transformed bryophyte cell according to claim 10, wherein said glycosylated polypeptide is selected from the group consisting of human insulin, preproinsulin, vascular endothelial growth factor (VEGF), proinsulin, glucagon, alpha-interferon, beta-interferon, gamma-interferon, blood-clotting factors VII, VIII, IX, X, XI, and XII, luteinising hormone, follicle stimulating hormone, epidermal growth factor, platelet-derived growth factor, granulocyte colony stimulating factor, prolactin, oxytocin, thyroid stimulating hormone, adrenocorticotropic hormone, calcitonin, parathyroid hormone, somatostatin, erythropoietin (EPO), beta-glucocerebrosidase, haemoglobin, serum albumin, and collagen.

12. A bryophyte plant or bryophyte tissue from *Physcomitrella patens* comprising a transformed bryophyte cell according to claim 9.

* * * * *